(12) United States Patent
Lee et al.

(10) Patent No.: US 11,065,348 B2
(45) Date of Patent: Jul. 20, 2021

(54) APPARATUS AND METHODS FOR MAKING RECOMBINANT PROTEIN-STABILIZED MONODISPERSE MICROBUBBLES

(71) Applicant: THE TRUSTEES OF THE UNIVERSITY OF PENNSYLVANIA, Philadelphia, PA (US)

(72) Inventors: Daeyeon Lee, Wynnewood, PA (US); Francesco Angile, Philadelphia, PA (US); Kevin Vargo, Philadelphia, PA (US); Daniel A. Hammer, Villanova, PA (US); Chandra M. Sehgal, Wayne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 360 days.

(21) Appl. No.: 15/320,177

(22) PCT Filed: Jun. 19, 2015

(86) PCT No.: PCT/US2015/036678
§ 371 (c)(1),
(2) Date: Dec. 19, 2016

(87) PCT Pub. No.: WO2015/196065
PCT Pub. Date: Dec. 23, 2015

(65) Prior Publication Data
US 2017/0119911 A1    May 4, 2017

Related U.S. Application Data

(60) Provisional application No. 62/014,451, filed on Jun. 19, 2014.

(51) Int. Cl.
| | |
|---|---|
| *A61B 8/00* | (2006.01) |
| *A61K 49/22* | (2006.01) |
| *B01F 13/00* | (2006.01) |
| *B01F 3/04* | (2006.01) |
| *A61B 8/08* | (2006.01) |
| *C07K 14/415* | (2006.01) |
| *A61N 7/00* | (2006.01) |
| *A61K 38/00* | (2006.01) |

(52) U.S. Cl.
CPC ............ *A61K 49/223* (2013.01); *A61B 8/481* (2013.01); *B01F 3/04503* (2013.01); *B01F 13/0062* (2013.01); *C07K 14/415* (2013.01); *A61K 38/00* (2013.01); *A61N 7/00* (2013.01); *B01F 13/0061* (2013.01); *B01F 2003/04858* (2013.01); *B01F 2215/0032* (2013.01); *B01F 2215/0034* (2013.01)

(58) Field of Classification Search
None
See application file for complete search history.

(56) References Cited

U.S. PATENT DOCUMENTS

| | | | | |
|---|---|---|---|---|
| 5,877,580 | A * | 3/1999 | Swierkowski | ....... B01J 19/0046 310/328 |
| 7,832,429 | B2 * | 11/2010 | Young | ................... B01F 5/0683 137/829 |
| 2008/0003142 | A1 | 1/2008 | Link et al. | |
| 2009/0130025 | A1 * | 5/2009 | Bohmer | ............... A61K 49/223 424/9.52 |
| 2011/0305761 | A1 | 12/2011 | Shum et al. | |
| 2012/0301903 | A1 | 11/2012 | Putnam et al. | |
| 2012/0328529 | A1 | 12/2012 | Lee et al. | |
| 2014/0105818 | A1 | 4/2014 | Hammer et al. | |

FOREIGN PATENT DOCUMENTS

WO    2009048532 A2    4/2009

OTHER PUBLICATIONS

Garstecki et al. (Appl. Phys. Lett. 2004, 85, 2649-2651).*
Wang et al. (Biomicrofluidics 2013, 7, 014103-1 to 014103-12).*
Choi et al. (Lab Chip 2010, 10, 456-461).*
Abate et al. (Appl. Phys. Lett. 92, 243509 (2008)).*
International Preliminary Report on Patentability with Written Opinion for International Application No. PCT/US2015/036678, dated Dec. 29, 2016, 9 pages.
International Search Report for International Application No. PCT/US2015/036678, dated Sep. 21, 2015, 2 pages.

* cited by examiner

*Primary Examiner* — Michael G. Hartley
*Assistant Examiner* — Melissa J Perreira
(74) *Attorney, Agent, or Firm* — BakerHostetler

(57) ABSTRACT

A microfluidic device for generating microbubbles includes a substrate and a microfluidic channel embedded in the substrate. The microfluidic channel includes a plurality of fluid inlets, at least one bubble formation outlet having a nozzle with an adjustable diameter, and a flow focusing junction in fluid communication with the plurality of fluid inlets and the bubble formation outlet. A method for mass producing monodisperse microbubbles with a microfluidic device includes supplying a flow of dispersed phase fluid into a first fluid inlet of a microfluidic channel, supplying a flow of continuous phase fluid into a second fluid inlet of the microfluidic channel, and adjusting a diameter of a nozzle to obtain a plurality of monodisperse microbubbles having a specified diameter.

9 Claims, 20 Drawing Sheets
Specification includes a Sequence Listing.

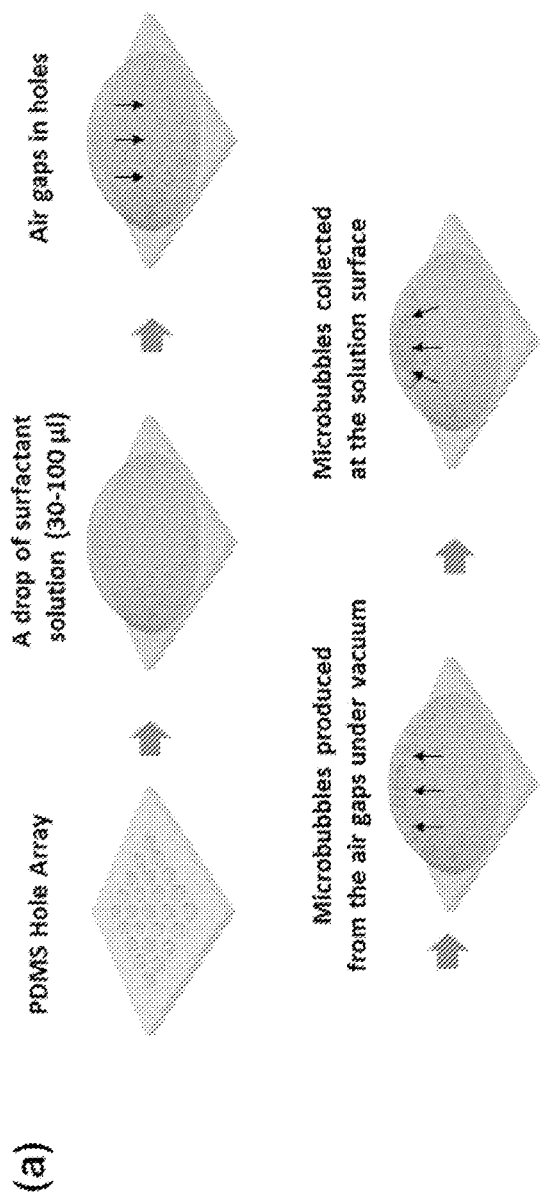
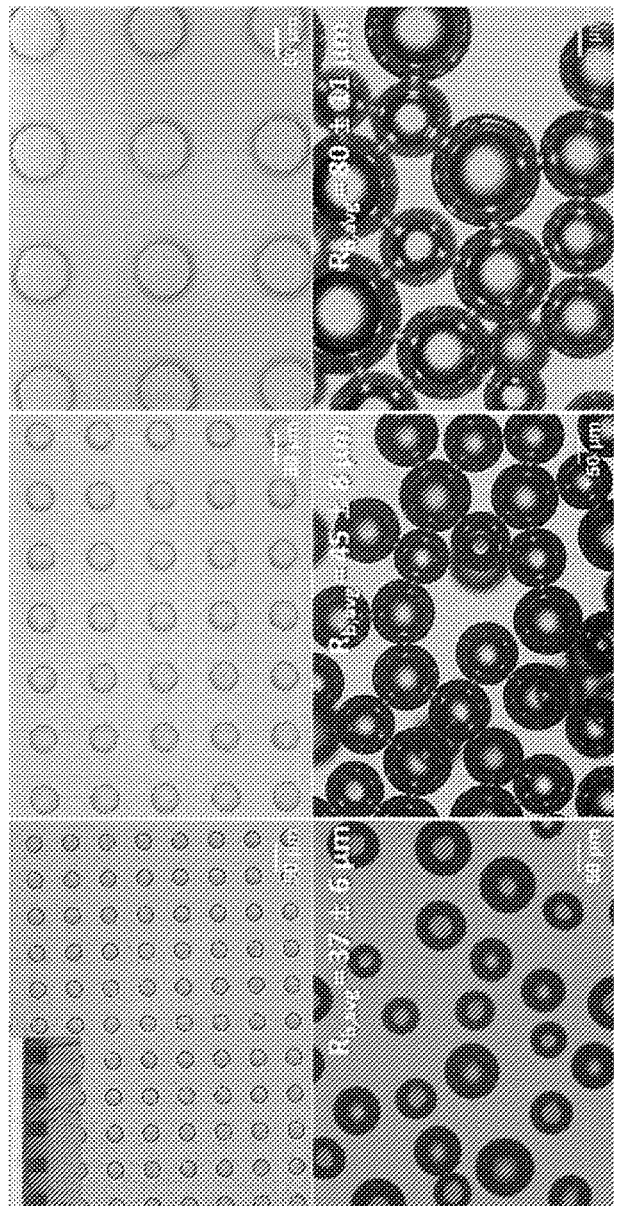
FIG. 15

```
                           SEQUENCE LISTING

<160> NUMBER OF SEQ ID NOS: 23

<210> SEQ ID NO 1
<211> LENGTH: 140
<212> TYPE: PRT
<213> ORGANISM: Artificial Sequence
<220> FEATURE:
<223> OTHER INFORMATION: Oleosin Variant

<400> SEQUENCE: 1

Gly Ser Ala Thr Thr Thr Tyr Asp Arg His His Val Thr Thr Thr Gln
1               5                   10                  15

Pro Gln Tyr Arg His Asp Gln His Thr Gly Asp Arg Leu Thr His Pro
            20                  25                  30

Gln Arg Gln Gln Gln Gly Pro Ser Thr Gly Lys Leu Ala Leu Gly Ala
        35                  40                  45

Thr Pro Leu Phe Gly Val Ile Gly Phe Ser Pro Val Ile Val Pro Ala
    50                  55                  60

Met Gly Ile Ala Ile Gly Leu Ala Gly Val Thr Gly Phe Gln Arg Asp
65                  70                  75                  80

Tyr Val Lys Gly Lys Leu Gln Asp Val Gly Glu Tyr Thr Gly Gln Lys
                85                  90                  95

Thr Lys Asp Leu Gly Gln Lys Ile Gln His Thr Ala His Glu Met Gly
            100                 105                 110

Asp Gln Gly Gln Gly Gln Gly Gln Gly Gly Lys Glu Gly Arg Lys
        115                 120                 125

Glu Gly Gly Lys Leu Glu His His His His His His
    130                 135                 140

<210> SEQ ID NO 2
<211> LENGTH: 378
<212> TYPE: PRT
<213> ORGANISM: Artificial Sequence
<220> FEATURE:
<223> OTHER INFORMATION: Oleosin Variant

<400> SEQUENCE: 2

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
```

```
                    130                 135                 140
Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                    165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
        210                 215                 220

Thr Ala Ala Gly Ile Thr Leu Gly Met Asp Glu Leu Tyr Lys Gly Ser
225                 230                 235                 240

Ala Thr Thr Thr Tyr Asp Arg His His Val Thr Thr Gln Pro Gln
                    245                 250                 255

Tyr Arg His Asp Gln His Thr Gly Asp Arg Leu Thr His Pro Gln Arg
                260                 265                 270

Gln Gln Gln Gly Pro Ser Thr Gly Lys Leu Ala Leu Gly Ala Thr Pro
            275                 280                 285

Leu Phe Gly Val Ile Gly Phe Ser Pro Val Ile Val Pro Ala Met Gly
        290                 295                 300

Ile Ala Ile Gly Leu Ala Gly Val Thr Gly Phe Gln Arg Asp Tyr Val
305                 310                 315                 320

Lys Gly Lys Leu Gln Asp Val Gly Glu Tyr Thr Gly Gln Lys Thr Lys
                    325                 330                 335

Asp Leu Gly Gln Lys Ile Gln His Thr Ala His Glu Met Gly Asp Gln
                340                 345                 350

Gly Gln Gly Gln Gly Gln Gly Gly Lys Glu Gly Arg Lys Glu Gly
            355                 360                 365

Gly Lys Leu Glu His His His His His
        370                 375

<210> SEQ ID NO 3
<211> LENGTH: 192
<212> TYPE: PRT
<213> ORGANISM: Artificial Sequence
<220> FEATURE:
<223> OTHER INFORMATION: Oleosin Variant

<400> SEQUENCE: 3

Met Ala Thr Thr Thr Tyr Asp Arg His His Val Thr Thr Gln Pro
1               5                   10                  15

Gln Tyr Arg His Asp Gln His Thr Gly Asp Arg Leu Thr His Pro Gln
                20                  25                  30

Arg Gln Gln Gln Gly Pro Ser Thr Gly Lys Ile Met Val Ile Met Ala
            35                  40                  45

Leu Leu Pro Ile Thr Gly Ile Leu Phe Gly Leu Ala Gly Ile Thr Leu
        50                  55                  60

Val Gly Thr Val Ile Gly Leu Ala Leu Ala Thr Pro Leu Phe Val Ile
65                  70                  75                  80

Phe Ser Pro Val Ile Val Pro Ala Met Ile Ala Ile Gly Leu Ala Val
                    85                  90                  95

Thr Gly Phe Leu Thr Ser Gly Thr Phe Gly Leu Thr Gly Leu Ser Ser
                100                 105                 110

Leu Ser Tyr Leu Phe Asn Met Val Arg Arg Ser Thr Met Ser Val Pro
```

```
            115                 120                 125
Val Gln Arg Asp Tyr Val Lys Gly Lys Leu Gln Asp Val Gly Glu Tyr
        130                 135                 140

Thr Gly Gln Lys Thr Lys Asp Leu Gly Gln Lys Ile Gln His Thr Ala
145                 150                 155                 160

His Glu Met Gly Asp Gln Gly Gln Gly Gln Gly Gln Gly Gly Gly Lys
                165                 170                 175

Glu Gly Arg Lys Glu Gly Gly Lys Leu Glu His His His His His His
        180                 185                 190

<210> SEQ ID NO 4
<211> LENGTH: 192
<212> TYPE: PRT
<213> ORGANISM: Artificial Sequence
<220> FEATURE:
<223> OTHER INFORMATION: Oleosin Variant
<220> FEATURE:
<221> NAME/KEY: MISC_FEATURE
<222> LOCATION: (43)..(129)
<223> OTHER INFORMATION: Xaa at positions 43 to 129 may be any
      naturally-occurring or artificial amino acid and up to 87 of them
      may be absent

<400> SEQUENCE: 4

Met Ala Thr Thr Thr Tyr Asp Arg His His Val Thr Thr Thr Gln Pro
1               5                   10                  15

Gln Tyr Arg His Asp Gln His Thr Gly Asp Arg Leu Thr His Pro Gln
                20                  25                  30

Arg Gln Gln Gln Gly Pro Ser Thr Gly Lys Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Gln Arg Asp Tyr Val Lys Gly Lys Leu Gln Asp Val Gly Glu Tyr
        130                 135                 140

Thr Gly Gln Lys Thr Lys Asp Leu Gly Gln Lys Ile Gln His Thr Ala
145                 150                 155                 160

His Glu Met Gly Asp Gln Gly Gln Gly Gln Gly Gln Gly Gly Gly Lys
                165                 170                 175

Glu Gly Arg Lys Glu Gly Gly Lys Leu Glu His His His His His His
        180                 185                 190

<210> SEQ ID NO 5
<211> LENGTH: 192
<212> TYPE: PRT
<213> ORGANISM: Artificial Sequence
<220> FEATURE:
<223> OTHER INFORMATION: Oleosin Variant
<220> FEATURE:
<221> NAME/KEY: MISC_FEATURE
<222> LOCATION: (1)..(42)
<223> OTHER INFORMATION: Xaa at positions 1 to 42 may be any naturally-
      occurring or artificial amino acid and up to 42 of them may be
      absent
```

<400> SEQUENCE: 5

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Ile Met Val Ile Met Ala
        35                  40                  45

Leu Leu Pro Ile Thr Gly Ile Leu Phe Gly Leu Ala Gly Ile Thr Leu
    50                  55                  60

Val Gly Thr Val Ile Gly Leu Ala Leu Ala Thr Pro Leu Phe Val Ile
65                  70                  75                  80

Phe Ser Pro Val Ile Val Pro Ala Met Ile Ala Ile Gly Leu Ala Val
                85                  90                  95

Thr Gly Phe Leu Thr Ser Gly Thr Phe Gly Leu Thr Gly Leu Ser Ser
                100                 105                 110

Leu Ser Tyr Leu Phe Asn Met Val Arg Arg Ser Thr Met Ser Val Pro
            115                 120                 125

Val Gln Arg Asp Tyr Val Lys Gly Lys Leu Gln Asp Val Gly Glu Tyr
130                 135                 140

Thr Gly Gln Lys Thr Lys Asp Leu Gly Gln Lys Ile Gln His Thr Ala
145                 150                 155                 160

His Glu Met Gly Asp Gln Gly Gln Gly Gln Gly Gln Gly Gly Gly Lys
                165                 170                 175

Glu Gly Arg Lys Glu Gly Gly Lys Leu Glu His His His His His His
            180                 185                 190
```

<210> SEQ ID NO 6
<211> LENGTH: 192
<212> TYPE: PRT
<213> ORGANISM: Artificial Sequence
<220> FEATURE:
<223> OTHER INFORMATION: Oleosin Variant
<220> FEATURE:
<221> NAME/KEY: MISC_FEATURE
<222> LOCATION: (130)..(192)
<223> OTHER INFORMATION: Xaa at positions 130 to 192 may be any
      naturally-occurring or artificial amino acid and up to 63 of them
      may be absent

<400> SEQUENCE: 6

```
Met Ala Thr Thr Thr Tyr Asp Arg His His Val Thr Thr Gln Pro
1               5                   10                  15

Gln Tyr Arg His Asp Gln His Thr Gly Asp Arg Leu Thr His Pro Gln
            20                  25                  30

Arg Gln Gln Gln Gly Pro Ser Thr Gly Lys Ile Met Val Ile Met Ala
        35                  40                  45

Leu Leu Pro Ile Thr Gly Ile Leu Phe Gly Leu Ala Gly Ile Thr Leu
    50                  55                  60

Val Gly Thr Val Ile Gly Leu Ala Leu Ala Thr Pro Leu Phe Val Ile
65                  70                  75                  80

Phe Ser Pro Val Ile Val Pro Ala Met Ile Ala Ile Gly Leu Ala Val
                85                  90                  95

Thr Gly Phe Leu Thr Ser Gly Thr Phe Gly Leu Thr Gly Leu Ser Ser
                100                 105                 110

Leu Ser Tyr Leu Phe Asn Met Val Arg Arg Ser Thr Met Ser Val Pro
            115                 120                 125
```

```
Val Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
180                 185                 190

<210> SEQ ID NO 7
<211> LENGTH: 192
<212> TYPE: PRT
<213> ORGANISM: Artificial Sequence
<220> FEATURE:
<223> OTHER INFORMATION: Oleosin Variant
<220> FEATURE:
<221> NAME/KEY: MISC_FEATURE
<222> LOCATION: (1)..(129)
<223> OTHER INFORMATION: Xaa at positions 1 to 129 may be any naturally-
      occurring or artificial amino acid and up to 129 of them may be
      absent

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Gln Arg Asp Tyr Val Lys Gly Lys Leu Gln Asp Val Gly Glu Tyr
    130                 135                 140

Thr Gly Gln Lys Thr Lys Asp Leu Gly Gln Lys Ile Gln His Thr Ala
145                 150                 155                 160

His Glu Met Gly Asp Gln Gly Gln Gly Gln Gly Gly Lys
                165                 170                 175

Glu Gly Arg Lys Glu Gly Gly Lys Leu Glu His His His His His
            180                 185                 190

<210> SEQ ID NO 8
<211> LENGTH: 192
<212> TYPE: PRT
<213> ORGANISM: Artificial Sequence
<220> FEATURE:
<223> OTHER INFORMATION: Oleosin Variant
<220> FEATURE:
<221> NAME/KEY: MISC_FEATURE
<222> LOCATION: (43)..(192)
<223> OTHER INFORMATION: Xaa at positions 43 to 192 may be any
      naturally-occurring or artificial amino acid and up to 150 of them
      may be absent

<400> SEQUENCE: 8
```

```
Met Ala Thr Thr Thr Tyr Asp Arg His His Val Thr Thr Gln Pro
1               5                   10                  15

Gln Tyr Arg His Asp Gln His Thr Gly Asp Arg Leu Thr His Pro Gln
            20                  25                  30

Arg Gln Gln Gln Gly Pro Ser Thr Gly Lys Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

<210> SEQ ID NO 9
<211> LENGTH: 192
<212> TYPE: PRT
<213> ORGANISM: Artificial Sequence
<220> FEATURE:
<223> OTHER INFORMATION: Oleosin Variant
<220> FEATURE:
<221> NAME/KEY: MISC_FEATURE
<222> LOCATION: (1)..(42)
<223> OTHER INFORMATION: Xaa at positions 1 to 42 may be any naturally-
      occurring or artificial amino acid and up to 42 of them may be
      absent
<220> FEATURE:
<221> NAME/KEY: MISC_FEATURE
<222> LOCATION: (130)..(192)
<223> OTHER INFORMATION: Xaa at positions 130 to 192 may be any
      naturally-occurring or artificial amino acid and up to 63 of them
      may be absent

<400> SEQUENCE: 9

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Ile Met Val Ile Met Ala
        35                  40                  45

Leu Leu Pro Ile Thr Gly Ile Leu Phe Gly Leu Ala Gly Ile Thr Leu
50                  55                  60

Val Gly Thr Val Ile Gly Leu Ala Leu Ala Thr Pro Leu Phe Val Ile
65                  70                  75                  80

Phe Ser Pro Val Ile Val Pro Ala Met Ile Ala Ile Gly Leu Ala Val
            85                  90                  95

Thr Gly Phe Leu Thr Ser Gly Thr Phe Gly Leu Thr Gly Leu Ser Ser
            100                 105                 110
```

```
Leu Ser Tyr Leu Phe Asn Met Val Arg Arg Ser Thr Met Ser Val Pro
        115                 120                 125

Val Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

<210> SEQ ID NO 10
<211> LENGTH: 134
<212> TYPE: PRT
<213> ORGANISM: Artificial Sequence
<220> FEATURE:
<223> OTHER INFORMATION: Oleosin Variant

<400> SEQUENCE: 10

Met Ala Thr Thr Thr Tyr Asp Arg His His Val Thr Thr Thr Gln Pro
1               5                   10                  15

Gln Tyr Arg His Asp Gln His Thr Gly Asp Arg Leu Thr His Pro Gln
            20                  25                  30

Arg Gln Gln Gln Gly Pro Ser Thr Gly Lys Leu Ala Leu Ala Thr Pro
        35                  40                  45

Leu Phe Val Ile Phe Ser Pro Val Ile Val Pro Ala Met Ile Ala Ile
    50                  55                  60

Gly Leu Ala Val Thr Gly Phe Gln Arg Asp Tyr Val Lys Gly Lys Leu
65                  70                  75                  80

Gln Asp Val Gly Glu Tyr Thr Gly Gln Lys Thr Lys Asp Leu Gly Gln
                85                  90                  95

Lys Ile Gln His Thr Ala His Glu Met Gly Asp Gln Gly Gln Gly Gln
            100                 105                 110

Gly Gln Gly Gly Gly Lys Glu Gly Arg Lys Glu Gly Gly Lys Leu Glu
        115                 120                 125

His His His His His His
    130

<210> SEQ ID NO 11
<211> LENGTH: 142
<212> TYPE: PRT
<213> ORGANISM: Artificial Sequence
<220> FEATURE:
<223> OTHER INFORMATION: Oleosin Variant

<400> SEQUENCE: 11

Gly Ser Glu Ala Thr Thr Thr Asn Asp Gln His His Val Thr Thr Thr
1               5                   10                  15

Gln Pro Gln Asp Gln His Asp Gln His Thr Gly Asp Gln Leu Thr His
            20                  25                  30

Pro Gln Asp Gln Gln Gly Pro Ser Thr Gly Glu Leu Ala Leu Gly
        35                  40                  45

Ala Thr Pro Leu Phe Gly Val Ile Gly Phe Ser Pro Val Ile Val Pro
    50                  55                  60

Ala Met Gly Ile Ala Ile Gly Leu Ala Gly Val Thr Gly Phe Gln Trp
65                  70                  75                  80

Gln Asp Asn Val Asn Gly Glu Leu Gln Asp Val Gly Glu Gln Thr Gly
```

```
                85                  90                  95
Gln Asn Thr Asn Asp Leu Gly Gln Gln Ile Gln His Thr Ala His Glu
            100                 105                 110

Met Gly Asp Gln Gly Gln Gly Gln Gly Gly Gly Asn Glu Gly
        115                 120                 125

Gln Asn Glu Gly Gly Asn His His His His Asp Asp
        130                 135                 140
```

<210> SEQ ID NO 12
<211> LENGTH: 140
<212> TYPE: PRT
<213> ORGANISM: Artificial Sequence
<220> FEATURE:
<223> OTHER INFORMATION: Oleosin Variant

<400> SEQUENCE: 12

```
Gly Ser Ala Thr Thr Thr Lys Asn Arg His His Val Thr Thr Thr Gln
1               5                   10                  15

Pro Gln Lys Arg His Asn Gln His Thr Gly Asn Arg Leu Thr His Pro
            20                  25                  30

Gln Arg Gln Gln Gln Gly Pro Ser Thr Gly Lys Leu Ala Leu Gly Ala
        35                  40                  45

Thr Pro Leu Phe Gly Val Ile Gly Phe Ser Pro Val Ile Val Pro Ala
    50                  55                  60

Met Gly Ile Ala Ile Gly Leu Ala Gly Val Thr Gly Phe Gln Trp Asn
65                  70                  75                  80

Lys Val Lys Gly Lys Leu Gln Asn Val Gly Gln Lys Thr Gly Gln Lys
                85                  90                  95

Thr Lys Asn Leu Gly Gln Lys Ile Gln His Thr Ala His Gln Met Gly
            100                 105                 110

Asn Gln Gly Gln Gly Gln Gly Gly Gly Lys Gln Gly Arg Lys
        115                 120                 125

Gln Gly Gly Lys Leu Glu His His His His His
        130                 135                 140
```

<210> SEQ ID NO 13
<211> LENGTH: 138
<212> TYPE: PRT
<213> ORGANISM: Artificial Sequence
<220> FEATURE:
<223> OTHER INFORMATION: Oleosin Variant
<220> FEATURE:
<221> NAME/KEY: MISC_FEATURE
<222> LOCATION: (133)..(138)
<223> OTHER INFORMATION: Xaa at positions 133 to 138 may be any
      naturally-occurring or artificial amino acid and up to 6 of them
      may be absent

<400> SEQUENCE: 13

```
Gly Ser Thr Thr Thr Tyr Asp Arg His His Val Thr Thr Thr Gln Pro
1               5                   10                  15

Gln Tyr Arg His Asp Gln His Thr Gly Asp Arg Leu Thr His Pro Gln
            20                  25                  30

Arg Gln Gln Gln Gly Pro Ser Thr Gly Lys Leu Ala Leu Ala Thr Pro
        35                  40                  45

Leu Phe Val Ile Phe Ser Pro Val Ile Val Pro Ala Met Ile Ala Ile
    50                  55                  60

Gly Leu Ala Val Thr Gly Phe Gln Arg Asp Tyr Val Lys Gly Lys Leu
65                  70                  75                  80
```

```
Gln Asp Val Gly Glu Tyr Thr Gly Gln Lys Thr Lys Asp Leu Gly Gln
            85                  90                  95

Lys Ile Gln His Thr Ala His Glu Met Gly Asp Gln Gly Gln Gly Gln
            100                 105                 110

Gly Gln Gly Gly Gly Lys Glu Gly Arg Lys Glu Gly Lys His His
        115                 120                 125

His His His His Xaa Xaa Xaa Xaa Xaa
        130                 135

<210> SEQ ID NO 14
<211> LENGTH: 60
<212> TYPE: PRT
<213> ORGANISM: Artificial Sequence
<220> FEATURE:
<223> OTHER INFORMATION: Her-2 Affibody

<400> SEQUENCE: 14

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys Leu Glu
    50                  55                  60

<210> SEQ ID NO 15
<211> LENGTH: 31
<212> TYPE: DNA
<213> ORGANISM: Artificial Sequence
<220> FEATURE:
<223> OTHER INFORMATION: Primer

<400> SEQUENCE: 15
aaggagatag gatccaccac aacctacgac c                              31

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
gcaccgagag cgagcttgcc ggttgagg                                  28

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
cctcaaccgg caagctcgct ctcggtgc                                  28

<210> SEQ ID NO 18
<211> LENGTH: 34
<212> TYPE: DNA
<213> ORGANISM: Artificial Sequence
<220> FEATURE:
<223> OTHER INFORMATION: Primer

<400> SEQUENCE: 18
```

-continued

```
ccttcacata atccctctga aacccggtaa cacc                                    34

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
ggtgttaccg ggtttcagag ggattatgtg aagg                                    34

<210> SEQ ID NO 20
<211> LENGTH: 33
<212> TYPE: DNA
<213> ORGANISM: Artificial Sequence
<220> FEATURE:
<223> OTHER INFORMATION: Primer

<400> SEQUENCE: 20
tatatgaatc tcgagtttcc ccccttcttt tcg                                     33

<210> SEQ ID NO 21
<211> LENGTH: 105
<212> TYPE: DNA
<213> ORGANISM: Artificial Sequence
<220> FEATURE:
<223> OTHER INFORMATION: Primer

<400> SEQUENCE: 21
ctcgctctcg gtgcgactcc gctgtttggt gttataggtt tcagccctgt tattgttcca        60
gcgatgggta tagcgattgg gcttgcgggt gttaccgggt ttcag                       105

<210> SEQ ID NO 22
<211> LENGTH: 31
<212> TYPE: DNA
<213> ORGANISM: Artificial Sequence
<220> FEATURE:
<223> OTHER INFORMATION: Primer

<400> SEQUENCE: 22
atcggtatac atatggtgag caagggcgag g                                       31

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23
atctaaaatg gatcccttgt acagctcg                                           28
```

APPARATUS AND METHODS FOR MAKING RECOMBINANT PROTEIN-STABILIZED MONODISPERSE MICROBUBBLES

CROSS-REFERENCE TO RELATED APPLICATIONS

This is the national phase of International Application No PCT/US2015/036678, filed 19 Jun. 2015, which claims priority to U.S. Provisional Application No. 62/014,051, filed 19 Jun. 2014. The disclosure of each of these applications is incorporated herein by reference in its entirety for all purposes.

GOVERNMENT RIGHTS

This invention was made with government support under grant numbers DMR1120901 and DMR1309556 awarded by the National Science Foundation. The government has certain rights in the invention.

FIELD OF THE INVENTION

This invention relates to the field of microfluidics and, more particularly, microbubbles as well as devices and processes for producing microbubbles.

BACKGROUND OF THE INVENTION

Microbubbles are used as contrast enhancing agents in ultrasound sonography and more recently have shown great potential as theranostic agents that enable both diagnostics and therapy. The use of microbubble contrast agents enables visualization of microvasculature which cannot be seen directly with Doppler ultrasound. The echogenicity of microbubbles coupled with their physical interactions with acoustic energy can also be used for triggered release of active agents, or for conversion of acoustic energy to thermal energy to enable therapeutic applications. For example, recent studies have shown that the insonation of microbubbles with low-intensity ultrasound can lead to a localized temperature increase, which in turn disrupts tumor vasculature (also known as anti-vascular ultrasound therapy), enabling minimally invasive procedure to disrupt cancerous tissues. These properties of microbubbles make them ideal candidates for theranostics; that is, the same microbubble agents can be used for diagnostics and therapeutic applications.

Conventional production methods undesirably lead to highly polydisperse microbubbles. Although some methods to fractionate microbubbles to enhance the uniformity of size have been reported, these techniques inevitably lead to loss of significant fraction of bubbles. Similarly, while the generation of monodisperse bubbles using microfluidic techniques has been reported, the size range of microbubbles that can be generated from such devices is somewhat limited.

Additionally, presently available microbubbles are typically stabilized with materials that offer limited possibilities in modifying the shell functionality for therapeutic applications.

These limitations compromise the effectiveness of microbubbles in ultrasound imaging and novel theranostic approaches such as targeted drug delivery and antivascular ultrasound therapy (AVUST). For example, polydisperse microbubbles may drastically reduce ultrasound image quality. With respect to drug transport, polydispersity may prevent a precise release of active agents.

SUMMARY OF THE INVENTION

Aspects of the invention relate to microbubbles, as well as devices and processes for producing microbubbles.

In accordance with one aspect, the invention provides a microfluidic device for generating microbubbles. The microfluidic device includes a substrate and a microfluidic channel embedded in the substrate. The microfluidic channel includes a plurality of fluid inlets, a flow focusing junction, and at least one bubble formation outlet, the at least one bubble formation outlet comprising a nozzle having an adjustable diameter.

In accordance with another aspect, the invention provides a method for mass producing monodisperse microbubbles with a microfluidic device. The method includes supplying a flow of dispersed phase fluid into a first fluid inlet of a microfluidic channel, supplying a flow of continuous phase fluid into a second fluid inlet of the microfluidic channel, and adjusting a diameter of a nozzle to obtain a plurality of monodisperse microbubbles having a specified diameter.

In accordance with yet another aspect, the invention provides a composition having a plurality of stable monodisperse microbubbles. Each microbubble includes a spherical shell having a mixture of oleosin and a surfactant, and an inner core having a gas.

In accordance with still another aspect, the invention provides a pharmaceutical composition having a plurality of stable monodisperse microbubbles. Each microbubble includes a spherical shell having a mixture of oleosin and a surfactant, and an inner core having a gas.

In accordance with still another aspect, the invention provides an ultrasound contrast enhancing agent having a plurality of stable monodisperse microbubbles. Each microbubble includes a spherical shell having a mixture of oleosin and a surfactant, and an inner core having a gas.

In accordance with a further aspect, the invention provides a recombinant protein having the amino acid sequence selected from SEQ ID NOS: 1-13.

In accordance with still a further aspect, the invention provides a pharmaceutical composition having a recombinant protein having the amino acid sequence selected from SEQ ID NOS: 1-13.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures:

FIG. 15a illustrates the generation of microbubbles by PDMS Hole Array Method.

FIG. 15b shows the average radius of the microbubbles (Rb,avg), as controlled by the PDMS hole sizes.

FIG. 16a shows microbubbles with F68 at 1 mg/ml.

FIG. 16b shows microbubbles with Oleosin-30G at 1 mg/ml.

FIG. 16c shows microbubbles with Oleosin-30G at 1 mg/ml and F68 at 10 mg/ml.

FIG. 16d shows microbubbles with Oleosin-30G at 1 mg/ml and F68 at 20 mg/ml.

FIG. 18a shows a real strain vs. tension for microbubbles with pure Oleosin-30G.

FIG. 18b shows a real strain vs. tension for microbubbles with Oleosin-30G+F68 at 10 mg/ml.

FIG. 18c shows a real strain vs. tension for microbubbles with Oleosin-30G+F68 at 20 mg/ml.

FIG. 18d illustrates the increase in slope as F68 concentration increases in solution.

FIG. 18e illustrates the amount of F68 vs. modulus.

FIG. 19a illustrates a real strain vs. tension with different kinds of Pluronic® surfactants.

FIG. 19b illustrates variations in modulus with different kinds of Pluronic® surfactants.

DETAILED DESCRIPTION OF THE INVENTION

Figure 1:
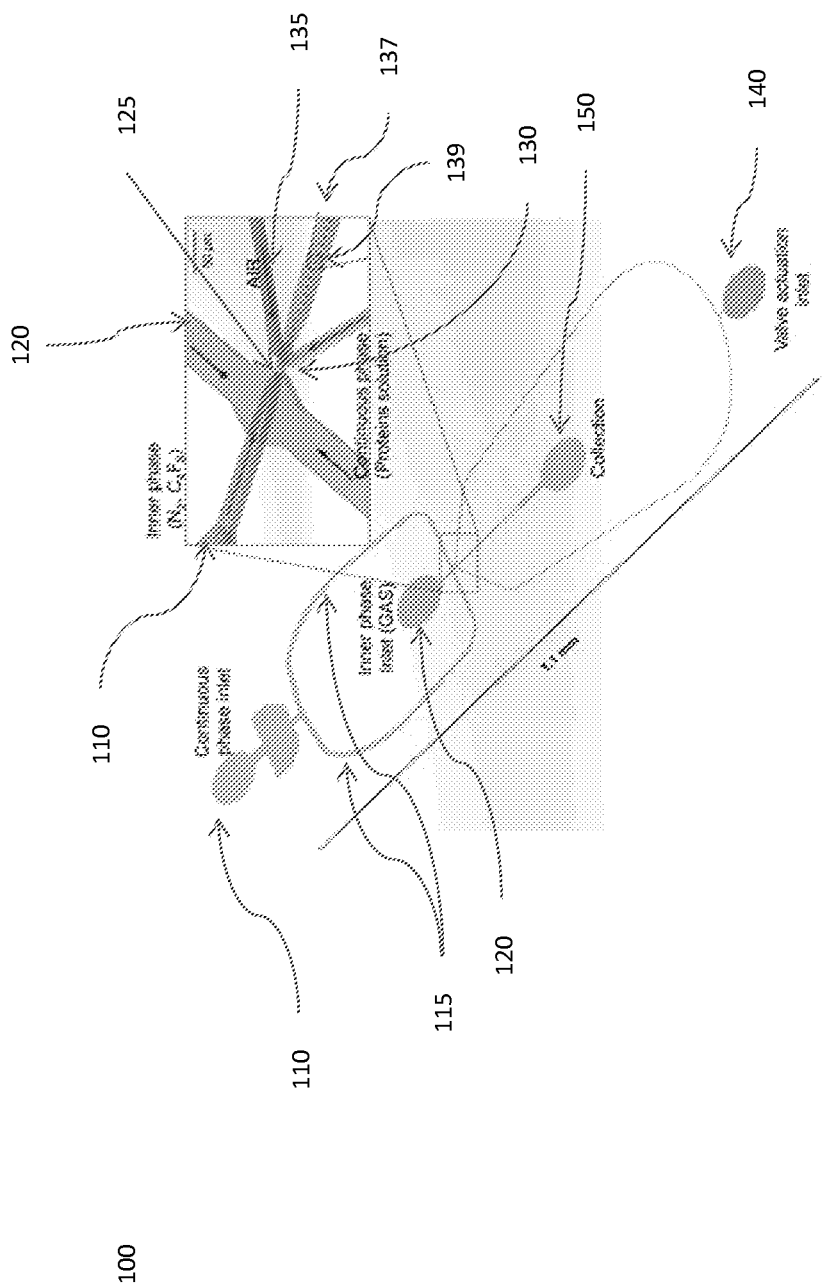
FIG. 1 is a schematic illustration of a microfluidic device according to principles of the present invention.

Aspects of the invention are directed to stable monodisperse microbubbles, methods for producing stable monodisperse microbubbles, stable monodisperse microbubbles produced by the inventive methods, and microfluidic devices for producing stable monodisperse microbubbles.

The inventors have recognized that it would be useful to provide stable and monodisperse protein-shelled microbubbles using a microfluidic flow focusing device. The inventors have also recognized that the use of a microfluidic device having an outlet nozzle with an adjustable diameter enables the production of highly monodisperse microbubbles, even at diameters below 10 μm. In particular, the inventors have found that the use of an fluid-actuated membrane valve enables precise control over the size of microbubbles while producing highly monodisperse microbubbles.

The inventors have also recognized that the use of particular recombinant proteins, such as oleosin, in the microbubble shell results in highly stable microbubbles. The inventors have further recognized that this use of, e.g., oleosin provides versatility in controlling the mechanical properties of the microbubble shell and adding specific ligands for targeted drug delivery applications through recombinant biotechnology.

As used herein, "monodisperse" means that the polydispersity index ("PDI") for a given collection of microbubbles is less than 5%. PDI is mathematically defined as PDI=s/n, wherein n denotes the average microbubble radius and s is the standard deviation of the bubble radii.

As used herein, "functionalized," "functionalization," "or "modified," when used to refer to oleosin, means that the oleosin has been altered using recombinant protein techniques to have different functionality and properties. For example, oleosin may be modified to include specific motifs or targeting ligands such as protease sites, adhesion peptides or affibodies. In one example, described in more detail below, green fluorescent protein (eGFP) is fused to the N-terminus of an oleosin mutant. One of ordinary skill in the art will understand that functionalization, however, may occur at any point of the oleosin or oleosin mutant. Oleosin may be functionalized using one or more of the following recombinant protein techniques: recombinant biotechnology, enzymatic linking, or direct covalent bonds. One of ordinary skill in the art will understand that other techniques may be used to achieve these alterations.

As used herein, "microfluidic channel" refers collectively to all channels in fluid communication with the continuous phase fluid inlet and the dispersed phase fluid inlet.

As used herein, "oleosin" refers to either a homogenous population of the same species of oleosin protein, a heterogeneous population of different species of oleosin proteins, or mutants thereof. For example, a substantial number of oleosin protein sequences, and associated nucleotide sequences encoding, are known from a large number of different plant species. Examples include, but are not limited to, oleosins from Arabidposis, canola, corn, rice, peanut, castor, soybean, flax, grape, cabbage, cotton, sunflower, sorghum and barley. While the present disclosure uses a sunflower seed oleosin gene for the purposes of illustrating certain principles of the invention, one of ordinary skill in the art will understand that the term "oleosin" is used broadly herein to refer not only to the explicitly described oleosin species and mutants, but to other oleosin species and oleosin mutants.

FIG. 1 shows a schematic perspective view of an exemplary embodiment of a microfluidic device 100 for generating monodisperse microbubbles according to aspects of the present invention. Microfluidic device 100 may be formed on a substrate. Exemplary substrates materials include polysiloxanes or carbon-based polymers including, but not limited to polydimethylsiloxane ("PDMS"), a polyacrlyamide, a polyacrylate, a polymethacrylate or a mixtures thereof.

Microfluidic device 100 includes at least two fluid inlets embedded in the substrate, including at least one continuous fluid inlet 110 and at least one dispersed fluid inlet 120. Continuous phase fluid inlet 110 and dispersed fluid inlet 120 are in fluid communication and may join one another at flow focusing junction 125. Bubble formation outlet 137 is similarly in fluid communication with continuous phase fluid inlet 110, dispersed phase fluid inlet 120, and flow focusing junction 125. Because each are in continuous fluid communication with each other, bubble formation outlet 137, continuous phase fluid inlet 110, dispersed phase fluid inlet 120, and flow focusing junction 125 are collectively referred to as a "microfluidic channel."

The microfluidic channel is, preferably, entirely enclosed within the substrate. Additionally, the microfluidic channel may, as depicted have different cross-sectional geometries at different locations. For example, continuous fluid supply channels 115 may have a rectangular cross-sectional geometry, but other geometries known to one of ordinary skill in the art will also be understood to be within the scope of the present invention. Other cross-sectional geometries include circular, octagonal, and other polygonal designs.

Each of bubble formation outlet 137, continuous phase fluid inlet 110, dispersed phase fluid inlet 120, and flow focusing junction 125 have a hydraulic diameter that is preferably smaller than 100 μm.

Continuous phase fluid inlet 110 supplies microfluidic device 100 with a controlled flow of a continuous phase fluid such as a liquid. In one embodiment, continuous fluid inlet 110 branches into two continuous fluid supply channels 115 which converge again at flow focusing junction 125.

Dispersed phase fluid inlet 120 supplies microfluidic device 100 with a controlled flow of a dispersed phase fluid such as a gas.

In an exemplary embodiment, continuous phase fluid inlet 110 and dispersed phase fluid inlet 120 discharge into flow focusing junction 125. Upon mixing of these inlets at flow focusing junction 125, microbubbles 139 are generated at nozzle 130 of bubble formation outlet 137. Microbubbles 139 then flow towards collection unit 150 for subsequent recovery.

Nozzle 130 preferably has an adjustable diameter. In particular, according to an aspect of this embodiment of the present invention, a user of microfluidic device 100 can dynamically tune the channel diameter of bubble formation outlet 137 at nozzle 130. In one embodiment, a fluid-actuated membrane valve 135 is used to constrict/expand nozzle 130 of bubble formation outlet 137 to obtain a desired diameter. The diameter of nozzle 130 may be adjusted through the application of pressure to valve 135. Pressure may be supplied to valve 135 via valve actuation inlet 140. In the depicted embodiment, fluid-actuated membrane valve 135 encircles nozzle 130, such that the application of pressure causes the valve 135 to inflate, thereby constricting the diameter of nozzle 130. Preferably, fluid-actuated membrane valve 135 is not in fluid communication with the microfluidic channel.

The use of fluid-actuated membrane valve 135 enables the control over the size of monodisperse bubbles. Both liquids and gases are suitable fluids to actuate membrane valve 135. In one embodiment, fluid-actuated membrane valve is an air-actuated membrane valve. This flexible design permits a user of microfluidic device 100 to tune the size of the microbubbles 139 without changing the continuous phase or dispersed phase flow rates, by only changing the size of nozzle 130 through the application of pressure to valve 135.

In one embodiment, the microfluidic device may be configured to have more than one bubble formation outlet, with each bubble formation outlet having a nozzle with an adjustable diameter.

Advantageously, from the perspective of manufacture, microfluidic device 100 may be constructed such that the microfluidic channel and valve 135 exist in the same plane. Doing so permits fabrication of microfluidic device 100 in a single layer mold. The use of a single layer membrane valve also overcomes the low resolution that is typically achieved by using polymeric photomasks (which are typically limited to ranges of microbubbles above 10 µm). However, the present invention is not limited to a planar flow focusing geometry, and one of ordinary skill in the art will understand that other geometries fall within the scope of the invention disclosed herein. For example other potential geometries include glass capillary devices, etched glass devices or 3-D PDMS devices.

Figure 2:
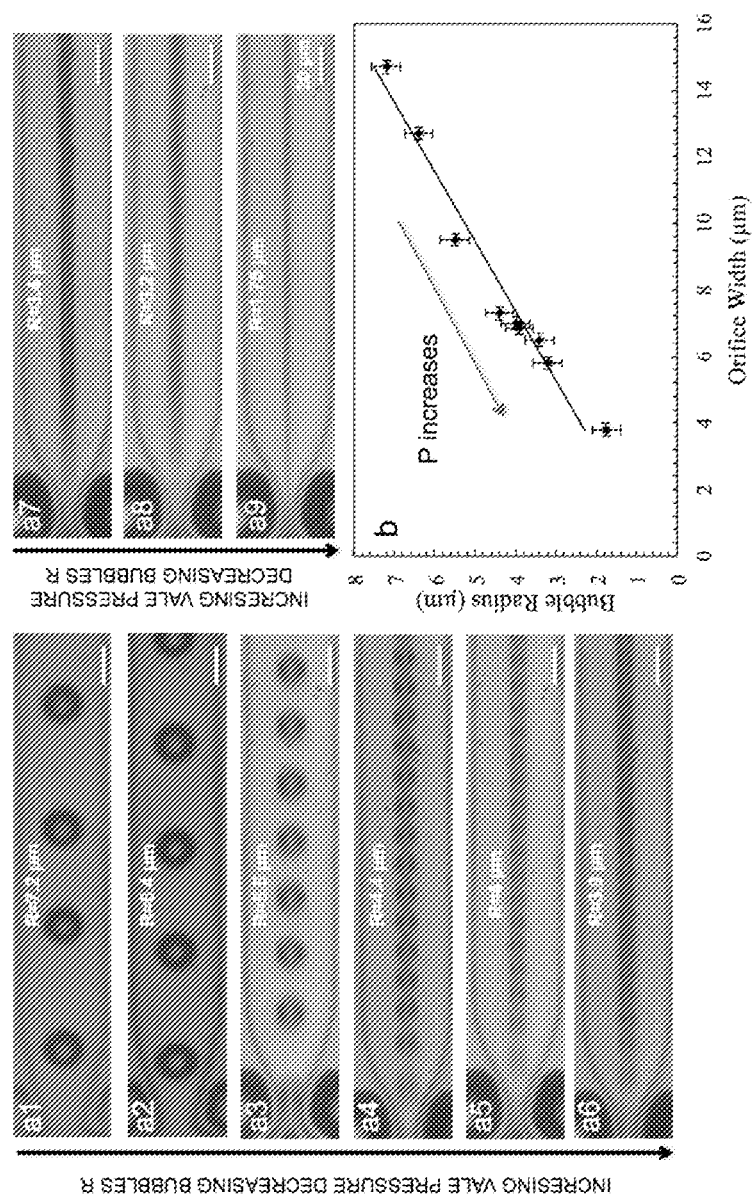
FIG. 2 is a micrograph of a microfluidic device according to principles of the present invention during the generation of microbubbles depicting the effect of changing the size of the nozzle on generate uniform microbubbles of different sizes.

As described above, microfluidic device 100 may be used to produce monodisperse microbubbles having tunable radii and a narrow size distribution. That is, microfluidic device 100 may be used to produce monodisperse microbubbles with radii ranging from 0.5 to 10 µm. By using a single microfluidic device according to aspects of the present invention, microbubbles having a broad range of radii may be generated, unlike most presently available flow-focusing microfluidic devices. In particular, as shown by FIG. 2, increasing the pressure that is applied to valve 145 decreases the orifice diameter of the nozzle 133 and, in turn, decreases the size of microbubbles. According to FIG. 2, the diameter of the microbubbles, $d_b$, decreases linearly with the width of the nozzle $w_n$. Thus, the size of microbubbles 139 may be precisely tuned by dynamically changing the dimension of nozzle 133 using valve 145.

Figure 3:
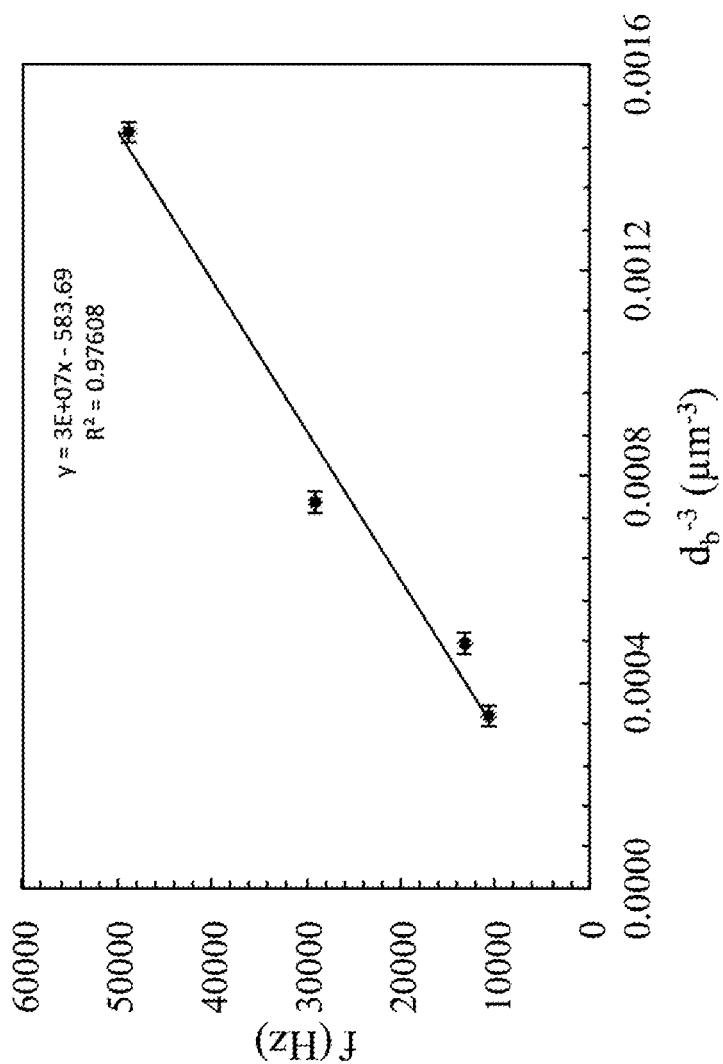
FIG. 3 is a graph depicting microbubbles generation frequency vs. volume of microbubbles according to principles of the present invention.

Microbubble generation frequency (f=the number of microbubbles generated per second) is shown, in FIG. 3, to be inversely proportional to the volume of microbubbles, e.g., $f \sim d_b^{-3}$. This trend indicates that the gas flow rate remains generally constant under varying nozzle size.

Figure 4:
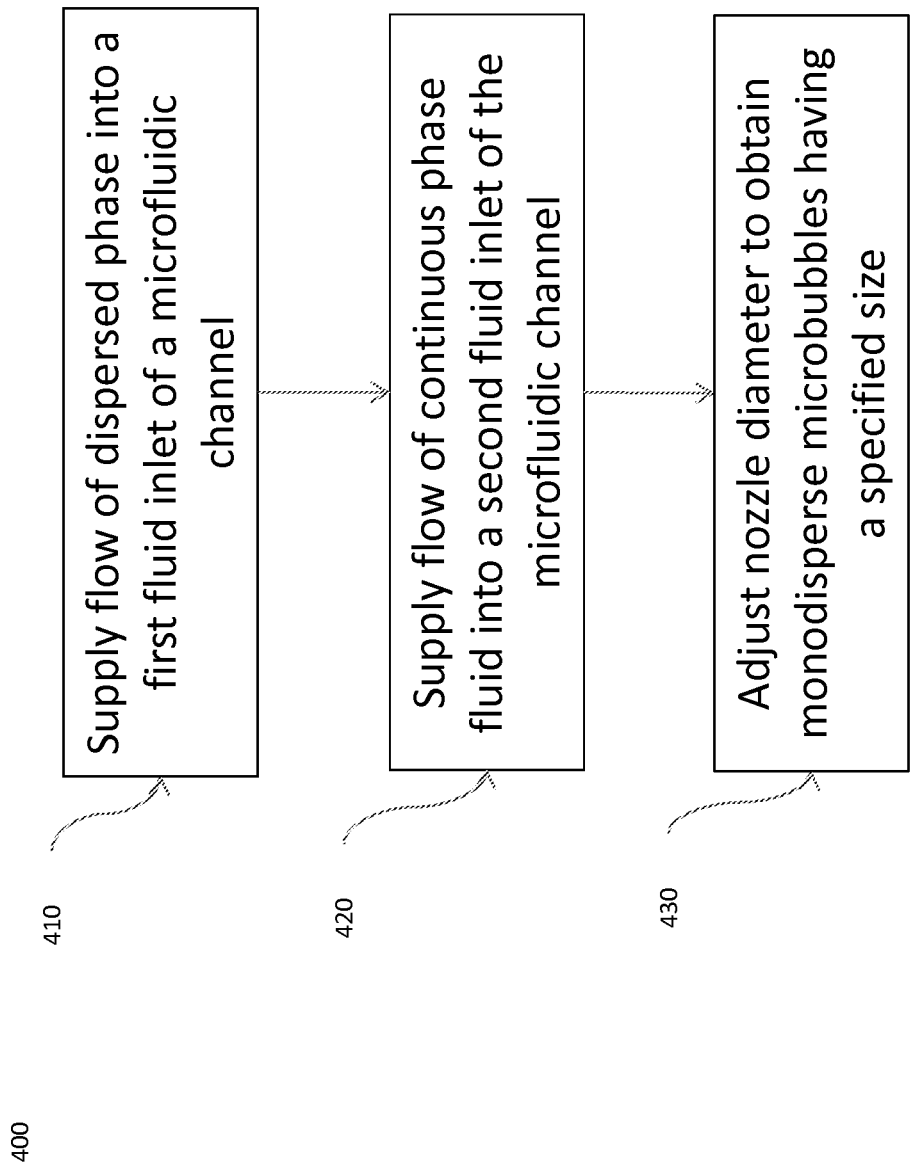
FIG. 4 is a flow diagram of a method for mass producing monodisperse microbubbles with a microfluidic device according to principles of the present invention.

Turning to FIG. 4, a flow diagram depicting selected steps of a process 400 for producing stable monodisperse microbubbles using a microfluidic device according to aspects of the invention is shown. It should be noted that, with respect to the methods described herein, it will be understood from the description herein that one or more steps may be omitted and/or performed out of the described sequence of the method (including simultaneously) while still achieving the desired result.

In step 410, a flow of a dispersed phase fluid is supplied into a first fluid inlet (e.g., dispersed phase fluid inlet 120; FIG. 1) of a microfluidic channel. In one embodiment, the dispersed phase fluid is a gas. The gas may be an inert gas. In particular, the gas may be one or more of nitrogen, carbon dioxide, helium, neon, xenon, argon, air, oxygen, sulfur hexafluoride, or heavy per fluorocarbon gases such as octafluorocyclobutane. For medical applications, gases having less solubility in water (e.g., nitrogen, air, sulfur hexafluoride and heavy perfluorocarbon gases) are preferred as this causes bubble dissolution to occur at a slower rate.

In step 420, a flow of a continuous phase fluid is supplied into a second fluid inlet (e.g., continuous phase fluid inlet 110; FIG. 1) of the microfluidic channel. In one embodiment, the continuous phase fluid is a liquid or liquid mixture. For example, and as described more fully below, the continuous phase fluid may be a mixture of a recombinant protein, such as oleosin, and a surfactant, such as a triblock copolymer.

In step 430, the diameter of a nozzle through which the mixture of dispersed phase and continuous phase fluids passes is adjusted to obtain a plurality of monodisperse microbubbles having a specified diameter. As described above, continuous phase fluid inlet 110 and dispersed phase fluid inlet 120 may discharge into flow focusing junction 125 that leads to nozzle 130 of bubble formation outlet 137. In the embodiment described above, an air-actuated membrane valve may be used to constrict/expand the nozzle to obtain a desired diameter. The fluid actuated membrane valve may encircle the nozzle, such that the application of pressure causes the valve to inflate, thereby constricting the diameter of nozzle.

In accordance with other aspects, a plurality of microbubbles is provided. The plurality of microbubbles may be obtained from the inventive methods described herein.

Figure 5:
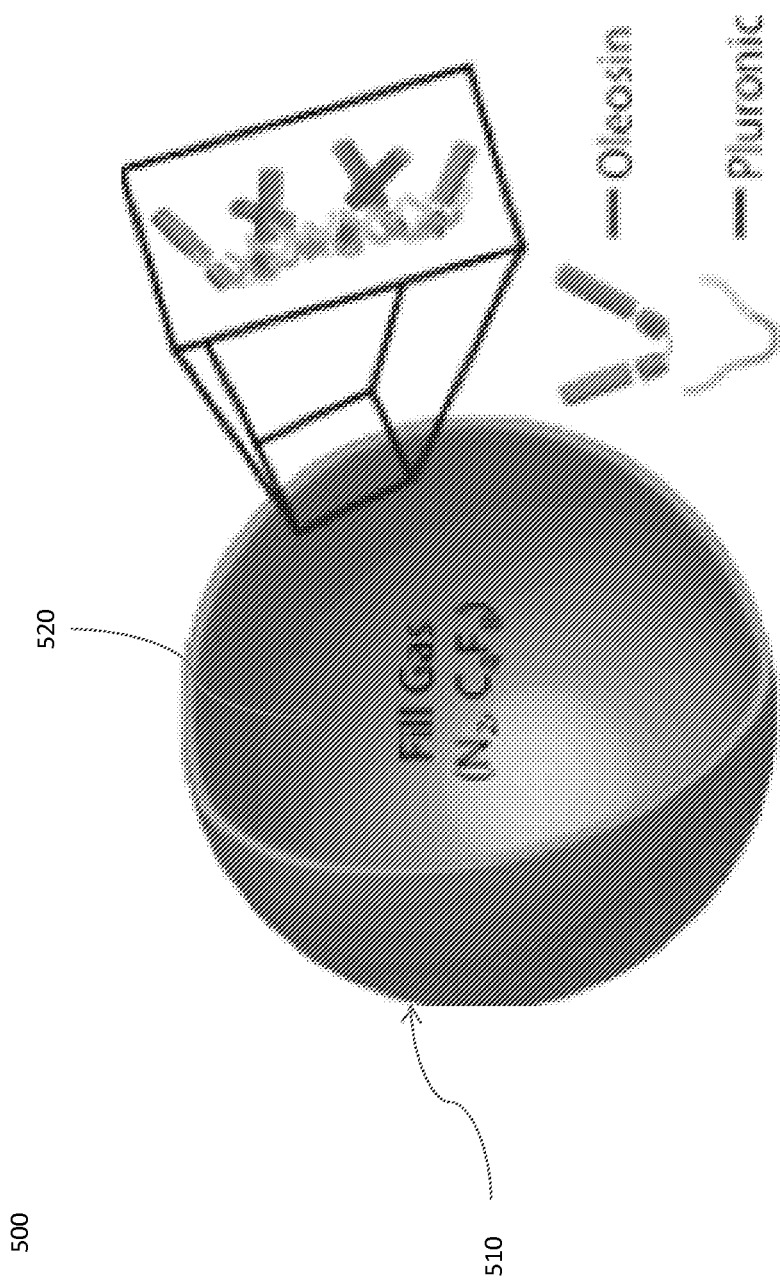
FIG. 5 is a schematic illustration of a microbubble according to principles of the present invention.

In accordance with other aspects, a composition including a plurality of stable monodisperse microbubbles is provided. Turning to FIG. 5, a microbubble 500 according to aspects of the present invention is shown. The microbubbles may be stabilized by incorporating an amphiphilic protein, oleosin, into spherical microbubble shell 510. Microbubbles incorporating oleosin are also echogenic and thus have value with respect to theranostic applications. Microbubbles composed of gaseous cores covered with stabilizing agents, such as oleosin, can drastically enhance the ultrasound signal because of their large compressibility, which leads to enhanced scattering of ultrasound.

Oleosins are structural proteins which are found in, and stabilize, vascular plant oil bodies. The protein has a natural amphiphilic structure (i.e., it includes both hydrophilic and hydrophobic groups). Oleosin proteins are composed of three distinctive domains: a central hydrophobic portion between N terminal and C-terminal amphiphilic arms. The central hydrophobic portion contains a proline knot which forces the protein into a hairpin structure. The elimination of a large portion of the hydrophobic domain and removal of the secondary structure in the protein backbone has been shown to yield a soluble oleosin mutant that naturally self-assembles into miscelles. This soluble oleosin mutant is named 42-30-63, which refers to the number of amino acids in each domain: the N-terminal arm, the central hydrophobic core, and the C-terminal hydrophilic arm, respectively. 42-30-63 may be produced by truncating the wildtype molecule without changes in the sequence of amino acids.

Figure 6:
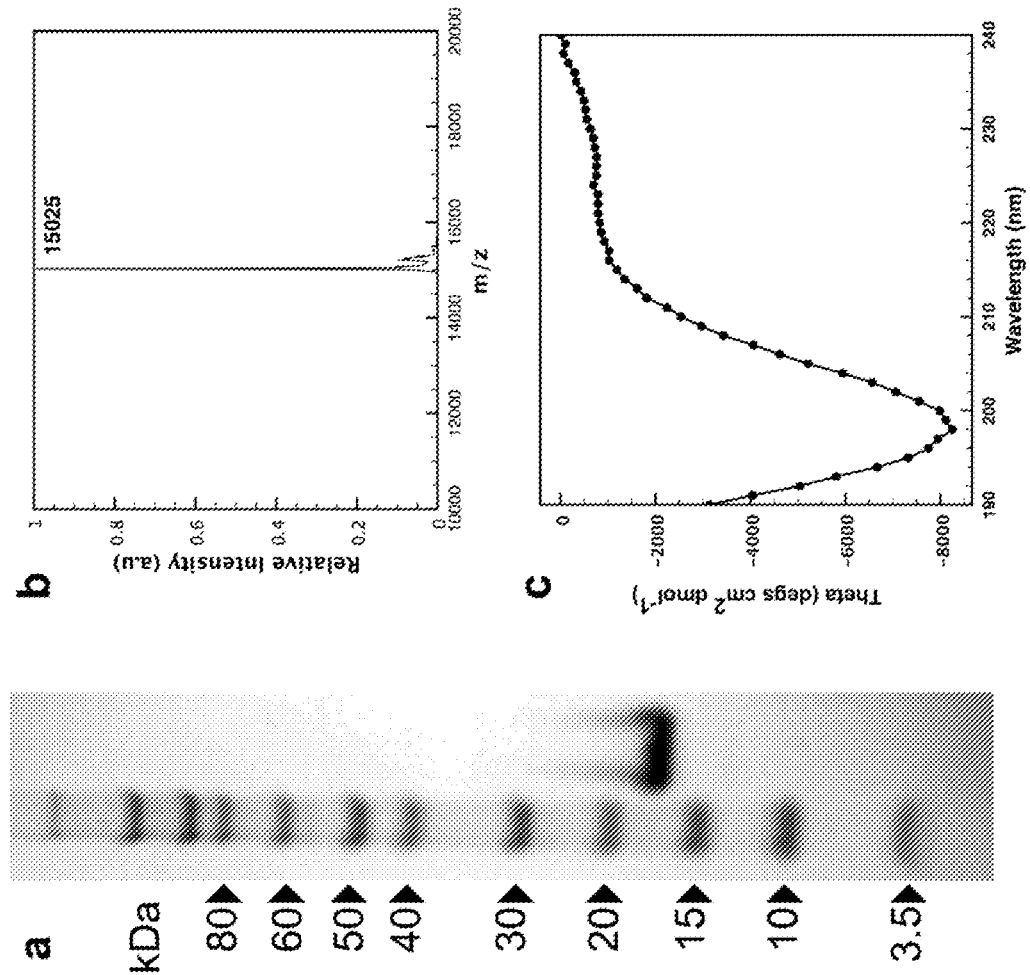
FIG. 6a is an SDS-PAGE gel for 42-30G-63 according to principles of the present invention.
FIG. 6b is a MADLI-TOF spectra confirming the molecular weight for 42-30G-63 according to principles of the present invention.
FIG. 6c is a far ultraviolet circular dichroism (UV CD) spectrum of 42-30G-63 according to principles of the present invention.

In one embodiment, a further modification of the 42-30-63 oleosin mutant is used in microbubble shell 510. In particular, the 42-30-63 oleosin mutant was further modified by inserting five glycines into the hydrophobic core, as shown by the amino acid sequence set forth in SEQ ID NO: 1, creating a mutant referred to as 42-30G-63. The addition of the five glycines desirably increases the protein expression, stability, and solubility while abolishing secondary structure, as shown by circular dichroism depicted in FIG. 6c. The protein was expressed in the Escherichia coli strain BL21 (DE3) with isopropyl β-D-1-thiogalactopyranoside (IPTG) induction.

In certain embodiments, the oleosin is functionalized. For example, as described above, oleosin may be modified to include specific targeting ligands such as binding motifs or affibodies. Microbubbles having these targeting ligands may be used to deliver an active pharmaceutical ingredient in higher concentrations to particular parts of a patient's body. For example, by functionalizing oleosin with specific targeting ligands via recombinant protein techniques, it will be possible to enable localized antivascular ultrasound therapy. Recombinant protein techniques may also be used to alter the molecular structure of oleosin (e.g., control the structure of the hydrophobic domain), thereby generating microbubble shells having different rheological properties. For example, alpha-helical domains, hydrogen bond networks, or crosslinking sites can be mutated into the hydrophobic core of oleosin increasing lateral interactions in the membrane potentially modifying elastic properties of the bubble shell.

Oleosin also provides the inventive microbubbles with versatility in that it enables the functionalization of microbubbles through recombinant biotechnology. By contrast, most microbubbles that are currently being developed use stabilizing agents such as phospholipids, proteins and polymers that undesirably cannot be easily modified to have, e.g., targeting ligands on the microbubble surface or to enable the modulation of the rheological properties of the stabilizing shells.

Spherical shell 510 may include a mixture of oleosin and one or more additional components, such as a surfactant. In one embodiment, oleosin is combined with a surfactant such as a triblock copolymer. For example, oleosin may be combined with a triblock copolymer of poly(ethylene glycol)-b-poly(propylene glycol)-b-poly(ethylene glycol) $((PEO)_n\text{-}(PPO)_m\text{-}(PEO)_n$ where n and m denote the number of ethylene oxide and propylene oxide repeat units, respectively; these polymers are also known as Pluronic and Polxamer). Other suitable surfactants include phospholipids, diblock copolymers, non-ionic surfactants, ionic surfactants. The combination of oleosin and surfactants has been found to have a particularly favorable effect on microbubble stability and generation.

Microbubble 500 also includes an inner core 520 filled with a dispersed phase, such as a gas. Inert gases are generally suitable for use in inner core 520. Exemplary gases include $N_2$ or $C_4F_8$ and $CO_2$. FIG. 5 depicts a mixture of $N_2$ and $C_4F_8$.

Figure 7:
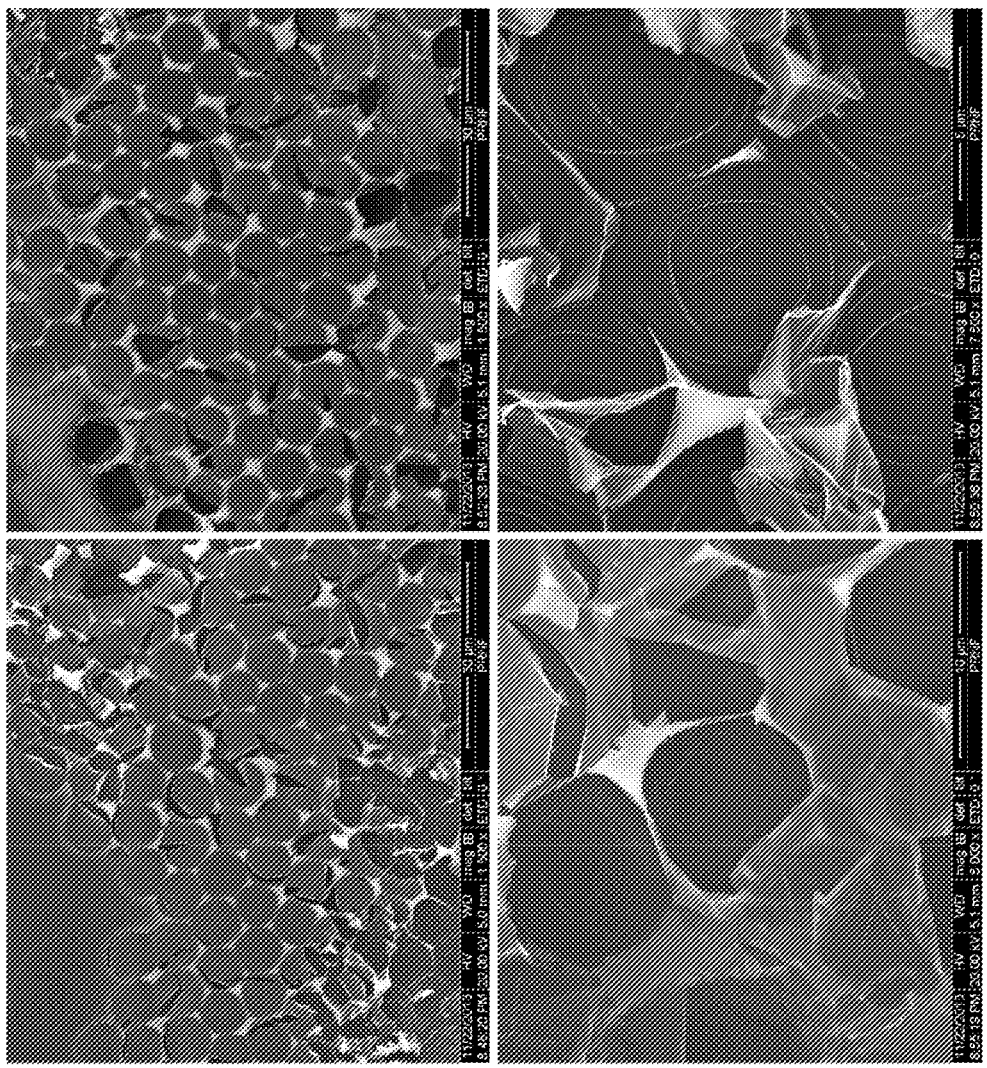
FIG. 7 is SEM images of dried microbubbles produced using a mixture of oleosin and $(PEO)_{78}$-$(PPO)_{30}$-$(PEO)_{78}$ according to principles of the present invention.

The composition of microbubbles may be dried through conventional methods (e.g., freeze drying), stored, and then rehydrated for later use. FIG. 7 depicts SEM images of dried microbubbles produced using a mixture of oleosin and $(PEO)_{78}\text{-}(PPO)_{30}\text{-}(PEO)_{78}$. Nearly full and rapid rehydration of the inventive microbubbles after storage in dry state for several months has been achieved.

In accordance with other aspects, a pharmaceutical composition having a plurality of stable monodisperse microbubbles is provided. Each microbubble includes a spherical shell having a mixture of oleosin and a surfactant, and an inner core filled with gas.

In accordance with other aspects, an ultrasound contrast enhancing agent having a plurality of stable monodisperse microbubbles is provided. Each microbubble includes a spherical shell having a mixture of oleosin and a surfactant, and an inner core filled with gas.

In accordance with other aspects, a recombinant protein having an amino acid sequence selected from the group consisting of SEQ ID NOS: 1-13 is provided.

According to particular embodiments, the oleosin described herein comprises, consists essentially of, or consists of an amino acid sequence selected from the group consisting of SEQ ID NOS: 1-13.

According to particular embodiments, one or more of the amino acids in SEQ ID NOS: 1-13 may be replaced with one or more different amino acids (e.g., between 1 and 10 amino acids).

According to particular embodiments, the oleosin may have at least 80% homology, or at least 85% homology, or at least 90% homology, or at least 95% homology, or at least 97% homology to any of the sequences selected from the group consisting of SEQ ID NOS: 1-13.

SEQ ID NO: 3 is a wild type oleosin sequence, with an N-terminal hydrophilic domain of 42 amino acids (starting with M), a central block of 87 amino acids (underlined), and a C-terminal block of 63 amino acids, including six H residues added for purification (his tag).

SEQ ID NOS: 4-9 are various truncations/modifications of SEQ ID NO: 3, wherein X may be any naturally-occurring or artificial amino acid and any number of the X amino acids may be absent (i.e., any one, more than one, or all of the X amino acids may be present or absent). The "central block" of amino acids is underlined in each of SEQ ID NOS: 3-10 shown below.

In SEQ ID. NO: 4, the N-terminal sequence is kept the same and the C-terminal sequence is kept the same, and the number of amino acids in the central (underlined) sequence can be changed, preferably from 87 down to 29 amino acids, or any number in between. X at positions 43 to 129 may be any naturally-occurring or artificial amino acid and up to 87 of them may be absent.

In SEQ ID. NO: 5, the N-terminal sequence can be changed, preferably between 1 and 42 amino acids, the C-terminal sequence is kept the same, and the central (underlined) sequence is kept the same. X at positions 1 to 42 may be any naturally-occurring or artificial amino acid and up to 42 of them may be absent.

In SEQ ID. NO: 6, the N-terminal sequence is kept the same, the central (underlined) sequence is kept the same, and the C-terminal sequence can be changed, preferably between 1 and 63 amino acids. X at positions 130 to 192 may be any naturally-occurring or artificial amino acid and up to 63 of them may be absent.

In SEQ ID. NO: 7, only the C-terminal sequence is kept the same. X at positions 1 to 129 may be any naturally-occurring or artificial amino acid and up to 129 of them may be absent.

In SEQ ID. NO: 8, only the N-terminal sequence is kept the same. X at positions 43 to 192 may be any naturally-occurring or artificial amino acid and up to 150 of them may be absent.

In SEQ ID. NO: 9, only the central block is kept the same. X at positions 1 to 42 may be any naturally-occurring or artificial amino acid and up to 42 of them may be absent; and X at positions 130 to 192 may be any naturally-occurring or artificial amino acid and up to 63 of them may be absent.

In SEQ ID. NO: 10, the central block (underlined) of SEQ ID. NO: 3 is truncated to 29 amino acids.

In SEQ ID: NO: 11, N- and C-termini were modified with individual amino acids to make the sequences more negatively charged, called Oleosin(−).

In SEQ ID: NO: 12, N- and C-termini were modified with individual amino acids to make the sequences more positively charged, called Oleosin(+).

SEQ ID. NO: 13 is another oleosin sequence wherein X may be any naturally-occurring or artificial amino acid and any number of the X amino acids may be absent (i.e., X at positions 133 to 138 may be any naturally-occurring or artificial amino acid and up to 6 of them may be absent). According to one embodiment, XXXXXX is RGDS (for binding a receptor).

According to particular embodiments, an affibody may be appended to either end of any of the oleosin sequences (SEQ ID NOS: 1-13) described herein (e.g., an affibody of length 5 to 80 amino acids). According to particular embodiments, the affibody is the Her-2 Affibody having SEQ ID NO: 14.

According to particular embodiments, any of the oleosin sequences described herein may be absent the starting methionine, due to methionine cleavage upon expression.

In accordance with other aspects, a pharmaceutical composition having a recombinant protein having the amino acid sequence selected from the group consisting of SEQ ID NOS: 1-13 is provided.

Oleosin Sequences

SEQ ID NO: 1
GSATTTYDRHHVTTTQPQYRHDQHTGDRLTHPQRQQQGPSTGKLALGATP
LFGVIGFSPVIVPAMGIAIGLAGVTGFQRDYVKGKLQDVGEYTGQKTKDL
GQKIQHTAHEMGDQGQGQGQGGGKEGRKEGGKLEHHHHHH

SEQ ID NO: 2
VSKGEELFTGVVPILVELDGDVNGHKFSVSGEGEGDATYGKLTLKFICTT
GKLPVPWPTLVTTLTYGVQCFSRYPDHMKQHDFFKSAMPEGYVQERTIFF
KDDGNYKTRAEVKFEGDTLVNRIELKGIDFKEDGNILGHKLEYNYNSHNV
YIMADKQKNGIKVNFKIRHNIEDGSVQLADHYQQNTPIGDGPVLLPDNHY
LSTQSALSKDPNEKRDHMVLLEFVTAAGITLGMDELYKGSATTTYDRHHV
TTTQPQYRHDQHTGDRLTHPQRQQQGPSTGKLALGATPLFGVIGFSPVIV
PAMGIAIGLAGVTGFQRDYVKGKLQDVGEYTGQKTKDLGQKIQHTAHEMG
DQGQGQGQGGGKEGRKEGGKLEHHHHHH

SEQ ID NO: 3
MATTTYDRHHVTTTQPQYRHDQHTGDRLTHPQRQQQGPSTGKIMVIMALL
PITGILFGLAGITLVGTVIGLALATPLFVIFSPVIVPAMIAIGLAVTGFL
TSGTFGLTGLSSLSYLFNMVRRSTMSVPVQRDYVKGKLQDVGEYTGQKTK
DLGQKIQHTAHEMGDQGQGQGQGGGKEGRKEGGKLEHHHHHH

SEQ ID NO: 4
MATTTYDRHHVTTTQPQYRHDQHTGDRLTHPQRQQQGPSTGKXXXXXXXX
XXXXXXXXXXXXXXXXXXXXXXXXXXXXXXXXXXXXXXXXXXXXXXXX
XXXXXXXXXXXXXXXXXXXXXXXXXXXXXXQRDYVKGKLQDVGEYTGQKTK
DLGQKIQHTAHEMGDQGQGQGQGGGKEGRKEGGKLEHHHHHH

SEQ ID NO: 5
XXXXXXXXXXXXXXXXXXXXXXXXXXXXXXXXXXXXXXXXXIMVIMAL
DLPITGILFGLAGITLVGTVIGLALATPLFVIFSPVIVPAMIAIGLAVTG
FLTSGTFGLTGLSSLSYLFNMVRRSTMSVPVQRDYVKGKLQDVGEYTGQK
TKDLGQKIQHTAHEMGDQGQGQGQGGGKEGRKEGGKLEHHHHHH

SEQ ID NO: 6
MATTTYDRHHVTTTQPQYRHDQHTGDRLTHPQRQQQGPSTGKIMVIMALL
PITGILFGLAGITLVGTVIGLALATPLFVIFSPVIVPAMIAIGLAVTGFL
TSGTFGLTGLSSLSYLFNMVRRSTMSVPVXXXXXXXXXXXXXXXXXXXX
XXXXXXXXXXXXXXXXXXXXXXXXXXXXXXXXXXXXXX

SEQ ID NO: 7
XXXXXXXXXXXXXXXXXXXXXXXXXXXXXXXXXXXXXXXXXXXXXXX
XXXXXXXXXXXXXXXXXXXXXXXXXXXXXXXXXXXXXXXXXXXXXXX
XXXXXXXXXXXXXXXXXXXXXXXXXXXXXXQRDYVKGKLQDVGEYTGQK
TKDLGQKIQHTAHEMGDQGQGQGQGGGKEGRKEGGKLEHHHHHH

SEQ ID NO: 8
MATTTYDRHHVTTTQPQYRHDQHTGDRLTHPQRQQQGPSTGKXXXXXXXX
XXXXXXXXXXXXXXXXXXXXXXXXXXXXXXXXXXXXXXXXXXXXXXXX
XXXXXXXXXXXXXXXXXXXXXXXXXXXXXXXXXXXXXXXXXXXX

SEQ ID NO: 9
XXXXXXXXXXXXXXXXXXXXXXXXXXXXXXXXXXXXXXXXXXXIMVIMAL
LPITGILFGLAGITLVGTVIGLALATPLFVIFSPVIVPAMIAIGLAVTGF
LTSGTFGLTGLSSLSYLFNMVRRSTMSVPVXXXXXXXXXXXXXXXXXXX
XXXXXXXXXXXXXXXXXXXXXXXXXXXXXXXXXXXXXXXXXX

SEQ ID NO: 10
MATTTYDRHHVTTTQPQYRHDQHTGDRLTHPQRQQQGPSTGKLALATPLF
VIFSPVIVPAMIAIGLAVTGFQRDYVKGKLQDVGEYTGQKTKDLGQKIQH
TAHEMGDQGQGQGQGGGKEGRKEGGKLEHHHHHH

SEQ ID NO: 11
GSEATTTNDQHHVTTTQPQDQHDQHTGDQLTHPQDQQQGPSTGELALGAT
PLFGVIGFSPVIVPAMGIAIGLAGVTGFQWQDNVNGELQDVGEQTGQNTN
DLGQQIQHTAHEMGDQGQGQGQGGGNEGQNEGGNHHHHHHDD

SEQ ID NO: 12
GSATTTKNRHHVTTTQPQKRHNQHTGNRLTHPQRQQQGPSTGKLALGATP
LFGVIGFSPVIVPAMGIAIGLAGVTGFQWNKVKGKLQNVGQKTGQKTKNL
GQKIQHTAHQMGNQGQGQGQGGGKQGRKQGGKLEHHHHHH

SEP ID NO: 13
GSTTTYDRHHVTTTQPQYRHDQHTGDRLTHPQRQQQGPSTGKLALATPLF
VIFSPVIVPAMIAIGLAVTGFQRDYVKGKLQDVGEYTGQKTKDLGQKIQH
TAHEMGDQGQGQGQGGGKEGRKEGGKHHHHHHXXXXXX (Her-2 Affibody)

SEQ ID NO: 14
VDNKFNKEMRNAYWEIALLPNLNNQQKRAFIRSLYDDPSQSANLLAEAKK
LNDAQAPKLE

EXAMPLES

The following examples are included to demonstrate the overall nature of the present invention. The examples further illustrate the improved results obtained by generating stable monodisperse microbubbles and by employing the microfluidic device and related processes according to principles of the present invention.

Example 1

Manufacture of a Microfluidic Device

Microfluidic flow focusing devices with expanding nozzle design according to FIG. 1 were fabricated using single layer soft lithography in PDMS. Negative photoresist SU-8 2010 (Microchem, Newton, Mass.), thinned to a 3:1 ratio with SU-8 developer, was spin coated onto a clean silicon wafers to a thickness of 5 μm and patterned to UV light through a transparency photomask (CAD/Art Service, Bandon, Oreg.) using a Karl Suss MA4 Mask Aligner (SUSS MicroTec Inc., Sunnyvale, Calif.). To incorporate an fluid-actuated valve, single-layer membrane valves, described by A. R. Abate et al., Appl. Phys. Lett. 2009, 94, 023503, were used. The single layer membrane exists in the same plane as the microfluidic channel, which permitted fabrication of the entire microfluidic device in a single layer mold. Sylgard 184 poly(dimethylsiloxane) (Dow Corning, Midland, Mich.) was mixed with crosslinker (ratio 12:1), degassed thoroughly and poured onto the photoresist pattern, and cured for 1 hr at 65° C. to make the membrane highly compliant. The PDMS replica were peeled off the wafer and bonded to a PDMS membrane fabricated by spin coating PDMS on a glass slide after oxygen-plasma activation of both surfaces. Having a microchannel fully-enclosed in PDMS allows for more efficient use of the valve-membrane.

Example 2

Gene Creation and Protein Expression

The sunflower seed oleosin gene was provided as a gift from Dr. Beaudoin at Rothamsted Research, Hampshire, England. Multiple rounds of PCR were used to create the oleosin gene 42-30G-63 and eGFP 42-30G-63. Multiple rounds of PCR were used to create the oleosin gene 42-30G-63 and eGFP-42-30G-63. The following PCR primers were used to create the three domains, which were combined in a single PCR step: N-terminal hydrophilic S 5'-AAGGAGA-TAGGATCCACCACAACCTACGACC-3' (SEQ ID NO: 15), N-terminal hydrophilic AS 5'-GCACCGAGAGCGAGCTTGCCGGTFGAGG-3' (SEQ ID NO: 16), hydrophobic S 5'-CCTCAACCGGCAAGCTCGCTCTCGGTGC-3' (SEQ ID NO: 17), hydrophobic AS 5-CCTTCACATAATCCCTCT-GAAACCCGGTAACACC-3' (SEQ ID NO: 18), C-terminal hydrophilic S 5'-GGTGTTACCGGGTTTCAGAGGGAT-TATGTGAAGG-3' (SEQ ID NO: 19), C-terminal hydrophilic AS 5'-TATAT-GAATCTCGAGTTTCCCCCCTTCHTTTTCG-3' (SEQ ID NO: 20). The PCRs to create the hydrophilic portions were run with the soluble oleosin gene as the template and the hydrophobic domain PRC was run with the following oligo as the template: 5'-CTCGCTCTCGGTGCGACTCCGCTGTTTGGTGT-TATAGGITTCAGCCCTGTTATTGTTCCAGCGAT GGGTATAGCGATTGGGCTTGCGGGTGT-TACCGGGTTTCAG-3' (SEQ ID NO: 21). PCR was used to create the eGFP mutants using the following primers: eGFP S 5'-ATCGGTATACATATGGTGAGCAAGGGCGAGG-3' (SEQ ID NO: 22) and eGFP AS 5'-ATCTAAAATG-GATCCCTTGTACAGCTCG-3' (SEQ ID NO: 23) with pBamUK-eGFP as a template. The genes were inserted into the expression vector pBamUK, a pET series derivative constructed by the Duyne Laboratory (School of Medicine, University of Pennsylvania).

Mutants were confirmed through DNA sequencing prior to protein expression. pBamUK adds a 6-Histidine tag to the C-terminus of the protein for IMAC purification. Protein was expressed in the E. Coli strain BL21 DE3 (Stratagene) controlled by the lac promoter. Cultures were grown at 37° C. in Luria Bertani (LB) with kanamycin (50 µg ml$^{-1}$) until $OD_{600} \approx 0.7$-$0.9$. Protein expression is induced with isopropyl β-D-1-thiogalactopyranoside (IPTG) to a final concentration of 1.0 mM. Cells were harvested by centrifugation and cell pellets are frozen at −20° C. prior to purification.

Example 3

Protein Purification and Characterization

B-PER protein extraction agent (Fisher Scientific, Waltham, Mass.) was used for protein purification. Pellets were resuspended in B-PER (30 ml B-PER per liter of culture) and DNAse was added to a final concentration of 1 µg/ml. The resuspended pellets were centrifuged at 15,000 g for 15 minutes. The 42-30G-63 supernatant was discarded and the eGFP-42-30G-63 supernatant was applied to an equilibrated column and allowed to bind for >1 hour. The remaining inclusion body pellet of 42-30G-63 was suspended in denaturing buffer (8M urea, 50 mM phosphate buffer, 300 mM NaCl). The solution was centrifuged at 15,000 g for 15 minutes and the supernatant was added to an equilibrated Ni-NTA column (Hispur Ni-NTA resin, Thermo Scientific). The denatured 42-30G-63 was allowed to bind to the column for >1 hours and washed three times with denaturing wash buffer (denaturing buffer with 20 mM imidazole). 42-30G-63 refolding was accomplished by diluting the column 50 times with refolding buffer (50 mM phosphate buffer, 300 mM NaCl, 5% by volume glycerol, 4° C.) and rocked at 4° C. for >1 hr. Both mutants was washed extensively with wash buffer (50 mM phosphate buffer, 300 mM NaCl, 20 mM imadzole) and eluted in fractions with elution buffer (50 mM phosphate buffer, 300 mM NaCl, 300 mM imidazole).

Figure 8:
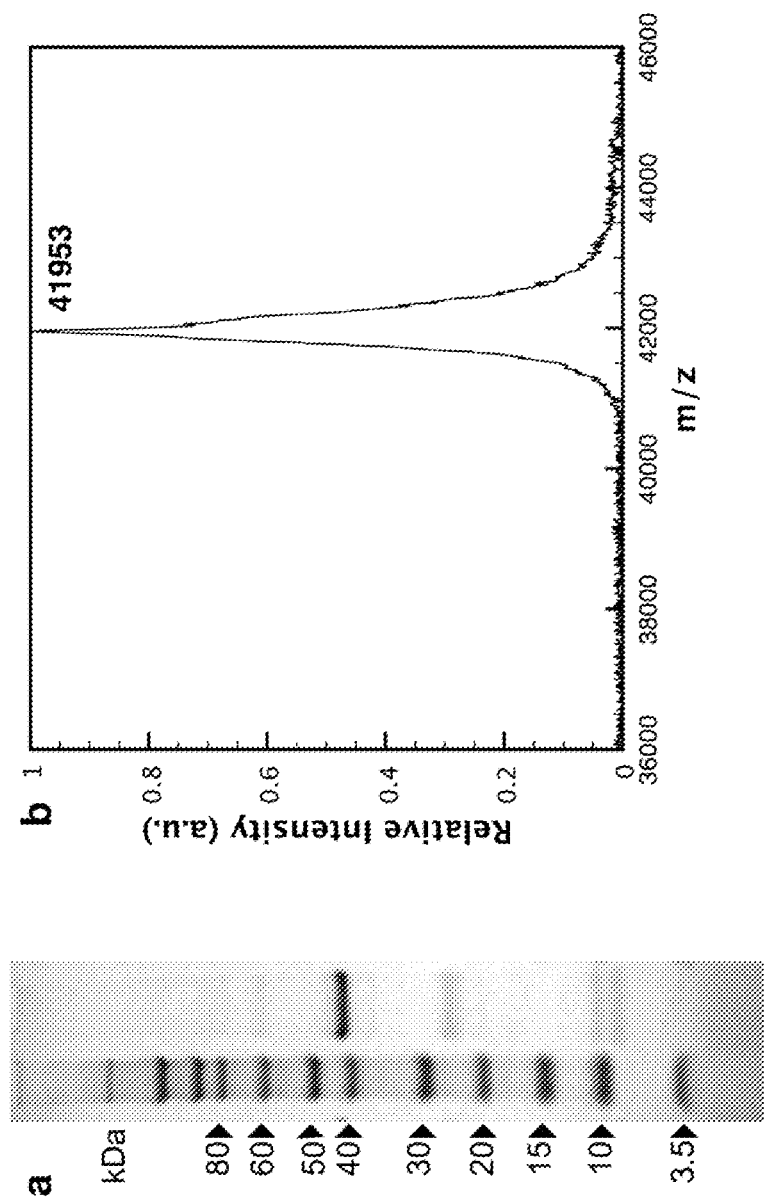
FIG. 8a is an SDS-PAGE gel for eGFP-42-30G-63 according to principles of the present invention.
FIG. 8b is a MADLI-TOF spectra confirming the molecular weight for eGFP-42-30G-63 according to principles of the present invention.

The concentration of purified protein was measured with a Nano-Drop 1000 (Thermo Scientific, Philadelphia, Pa.). Buffer exchange was completed with dialysis. All analysis was completed in PBS unless otherwise noted. To establish the purity of the proteins, SDS/PAGE gels were run on NuPAGE Novex 4-12% Bis-Tris mini gels (Invitrogen, Waltham, Mass.) in MES buffer. The gel was stained with SimplyBlue SafeStain (Invitrogen, Waltham, Mass.) following electrophoresis. The gel was destained overnight in water and imaged with a Kodak Gel Logic 100 Imaging System. Protein molecular weight was confirmed with MALDI-TOF. Sample spots were created with 0.5 µl protein in 1× PBS and 0.5 µl saturated sinapinic acid solution (50/50 acetonitrile/water+0.1% TFE). Spectra were collected on an Ultraflextreme MALDI-TOF (Bruker, Billerica, Mass.). FIG. 8 depicts the spectra for eGFP-42-30G-63. To measure the protein secondary structure, far-UV CD spectra were collected at 25° C. on an AVIV 410 spectrometer (AVIV Biomedical Inc., Lakewood Township, N.J.) using a 1 mm quartz cell. Protein concentration is 15 µM in 50 mM phosphate, 140 mM NaF. NaF is used to replace NaCl due to the strong absorbance of the Cl$^-$ ion.

Example 4

Initial Testing of Microfluidic Device

For the initial testing of the microfluidic device to control the size of microbubbles, nitrogen gas and a common surfactant, sodium dodecyl sulfate (SDS, Sigma-Aldrich, St Luis, Mo., USA), was used at a concentration of 20 mg mL$^{-1}$ in the aqueous phase to stabilize microbubbles. Monodisperse microbubbles were produced with radii ranging from approximately 2 to 10 µm for several hours without changes in the bubble size. Although SDS enables the investigation of microfluidic device performance, microbubbles formed using SDS are not stable upon collection.

To produce stable microbubbles with high monodispersity, size tunability and structural modularity, a structurally modified recombinant oleosin was used as the microbubble shell material. The 42-30G-63 protein expressed in the Escherichia coli strain BL21 (DE3) with isopropyl β-D-1-thiogalactopyranoside (IPTG) induction. Protein was purified using immobilized metal affinity chromatography through a 6-histidine tag on the C-terminus of the protein leading to highly purified products as shown in FIGS. 8a and 8b. Protein molecular weight is confirmed with SDS-polyacrylamide gel electrophoresis (SDS-PAGE) and matrix-assisted laser desorption/ionization-time of flight (MALDI-TOF) mass spectroscopy.

Figure 9:
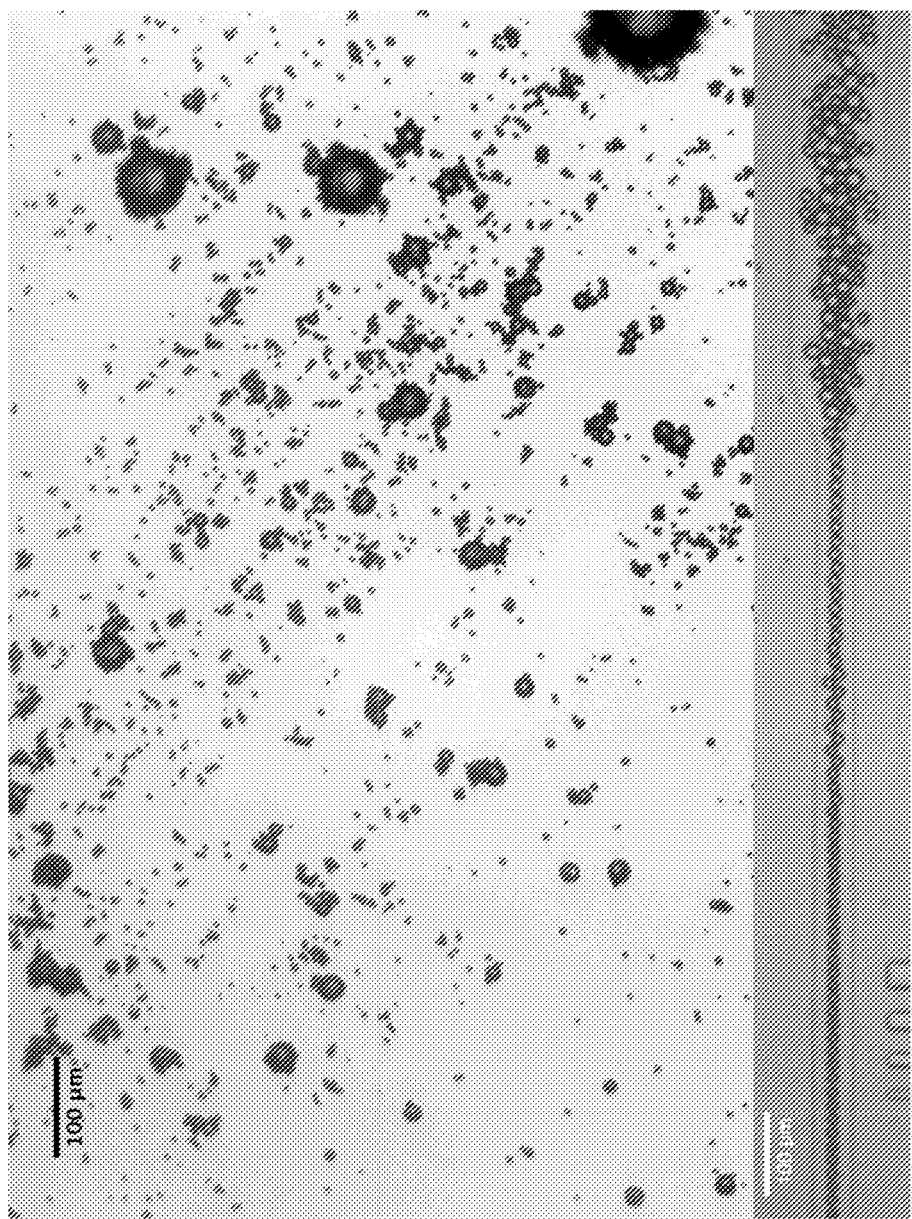
FIG. 9 is micrographs of microbubbles produced using the oleosin protein 42-30G-63 according to principles of the present invention.

When microbubbles are produced using oleosin at concentrations between 1-2 mg mL$^{-1}$, bubbles with radii above 10 µm are stable. During the generation of microbubbles with radii smaller than 10 µm, bubbles are observed to undergo coalescence within and outside of the microfluidic device as shown in FIG. 9. In addition, the relatively high surface tension between the liquid and the gas phases makes the generation of such microbubbles challenging, often resulting instability of microbubbles in the microfluidic device.

Figure 10:
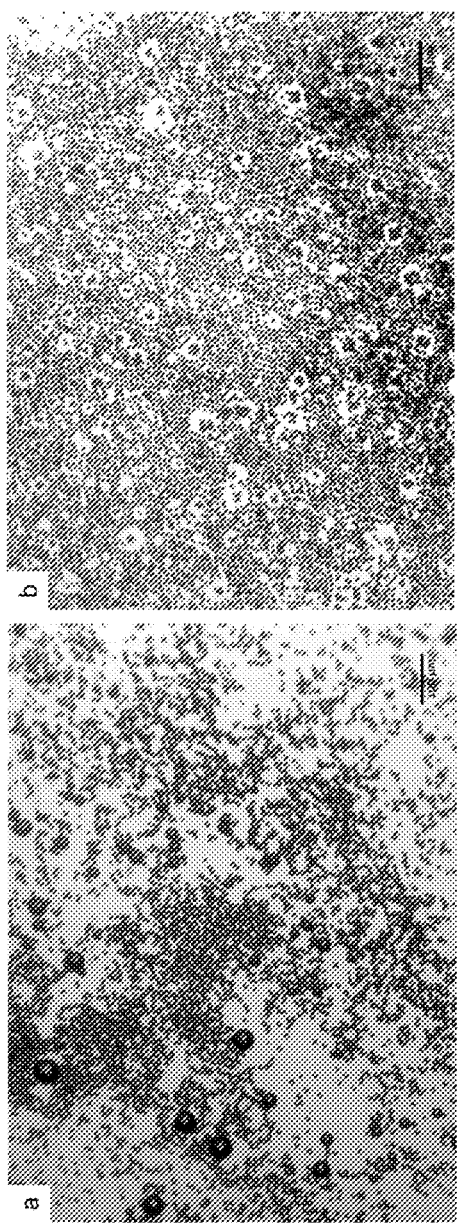
FIG. 10a is a micrograph of microbubbles produced using a mixture of oleosin and $(PEO)_{78}$-$(PPO)_{30}$-$(PEO)_{78}$ present upon tubing according to principles of the present invention.
FIG. 10b is a micrograph of microbubbles produced using a mixture of oleosin and $(PEO)_{78}$-$(PPO)_{30}$-$(PEO)_{78}$ 24 hours after collection according to principles of the present invention.

Poly(ethylene glycol)-b-poly(propylene glycol)-b-poly (ethylene glycol) triblock copolymers (($PEO)_n$-$(PPO)_m$-$(PEO)_n$ were added to the oleosin solution to test whether the production of microbubbles can be facilitated. Two different types of $(PEO)_n$-$(PPO)_m$-$(PEO)_n$ triblock copolymers: $(PEO)_{100}$-$(PPO)_{65}$-$(PEO)_{100}$ and $(PEO)_{78}$-$(PPO)_{30}$-$(PEO)_{78}$ were tested. When a mixture containing 1-2 mg mL$^{-1}$ oleosin and 5-20 mg mL$^{-1}$ $(PEO)_{100}$-$(PPO)_{65}$-$(PEO)_{100}$ (average molecular weight 12600) was used, monodisperse microbubbles were consistently generated at the nozzle; however, these microbubbles underwent significant coalescence upon collection. In contrast, when $(PEO)_{78}$-$(PPO)_{30}$-$(PEO)_{78}$ (average molecular weight 8400) was added to oleosin solutions, microbubbles were generated at the nozzle and very limited coalescence was observed upon collection. A suitable concentration for stable microbubble formation includes an aqueous phase containing 1 mg mL$^{-1}$ of oleosin and 10 mg mL$^{-1}$ of $(PEO)_{78}$-$(PPO)_{30}$-$(PEO)_{78}$. In the samples that are collected through polyethylene tubing, a small number of fairly large bubbles (>20 μm in diameter) were observed. Although the physical mechanism behind the appearance of these large bubbles is not known, their number fraction is extremely small, typically less than 1%. Interestingly, these large bubbles disappear completely approximately 24 h after collection, leaving behind a collection of highly monodisperse microbubbles as shown in FIGS. 10a and b.

Figure 11:
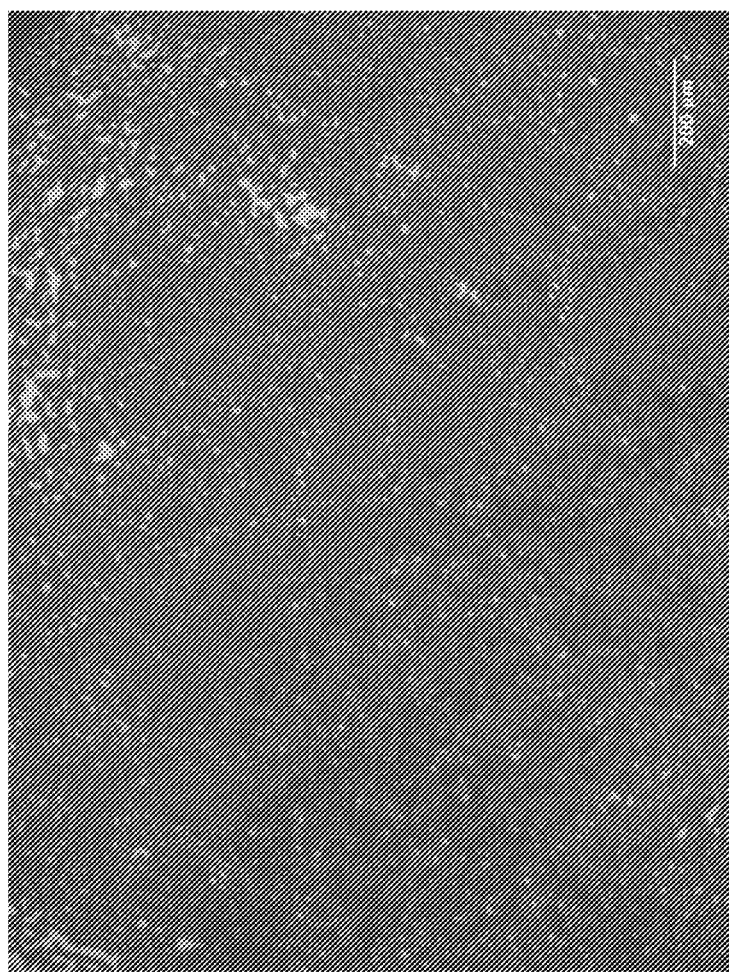
FIG. 11 is a micrograph of monodisperse microbubbles produced using a mixture of oleosin and $(PEO)_{78}$-$(PPO)_{30}$-$(PEO)_{78}$ and collected into a well in the PDMS device without the use of plastic tubing according to principles of the present invention.
Figure 12:
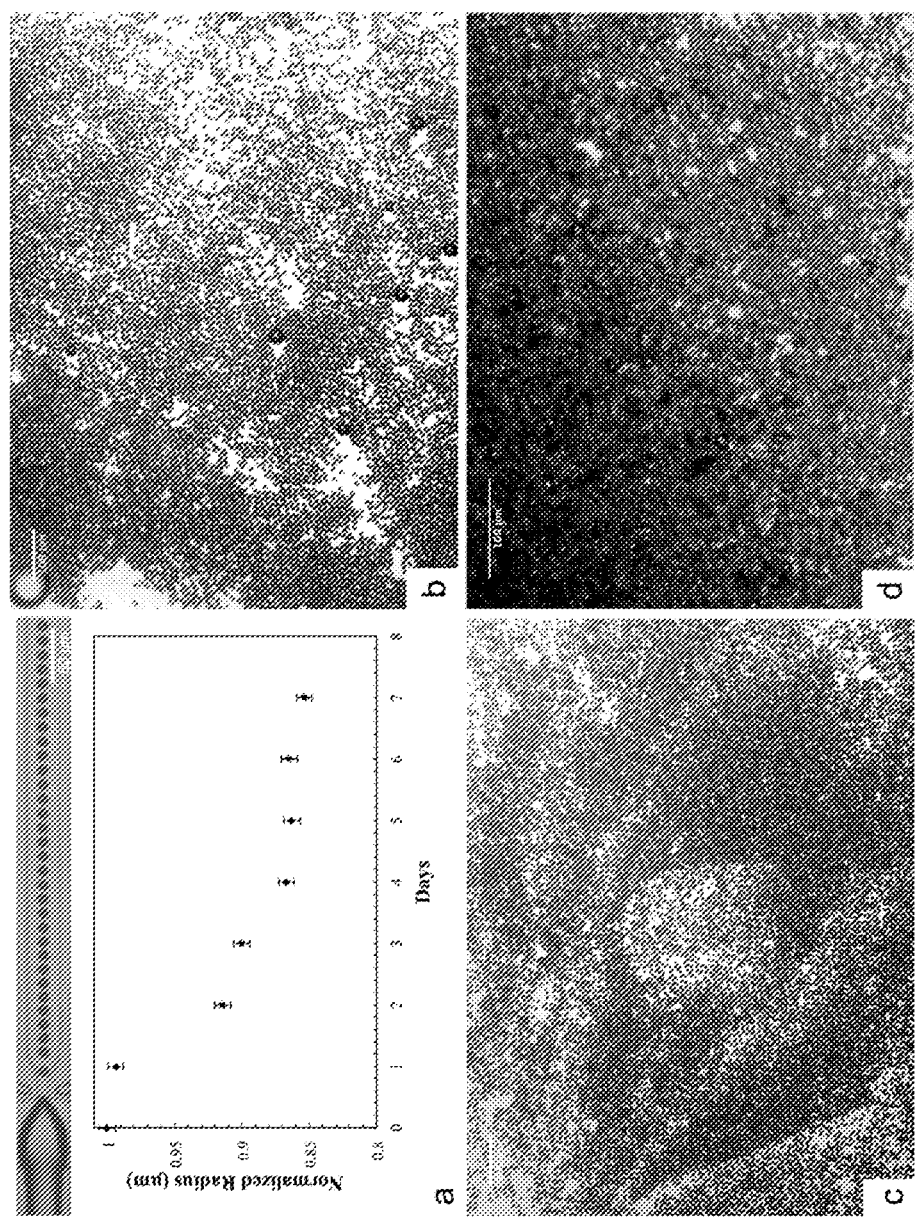
FIG. 12a is a graph depicting the size of microbubbles over time according to principles of the present invention.
FIG. 12b is a micrograph depicting the size of microbubbles upon collection according to principles of the present invention.
FIG. 12c is a micrograph depicting the size of microbubbles 7 days after collection according to principles of the present invention.
FIG. 12d is a micrograph depicting the size of microbubbles 24 days after collection according to principles of the present invention.
Figure 13:
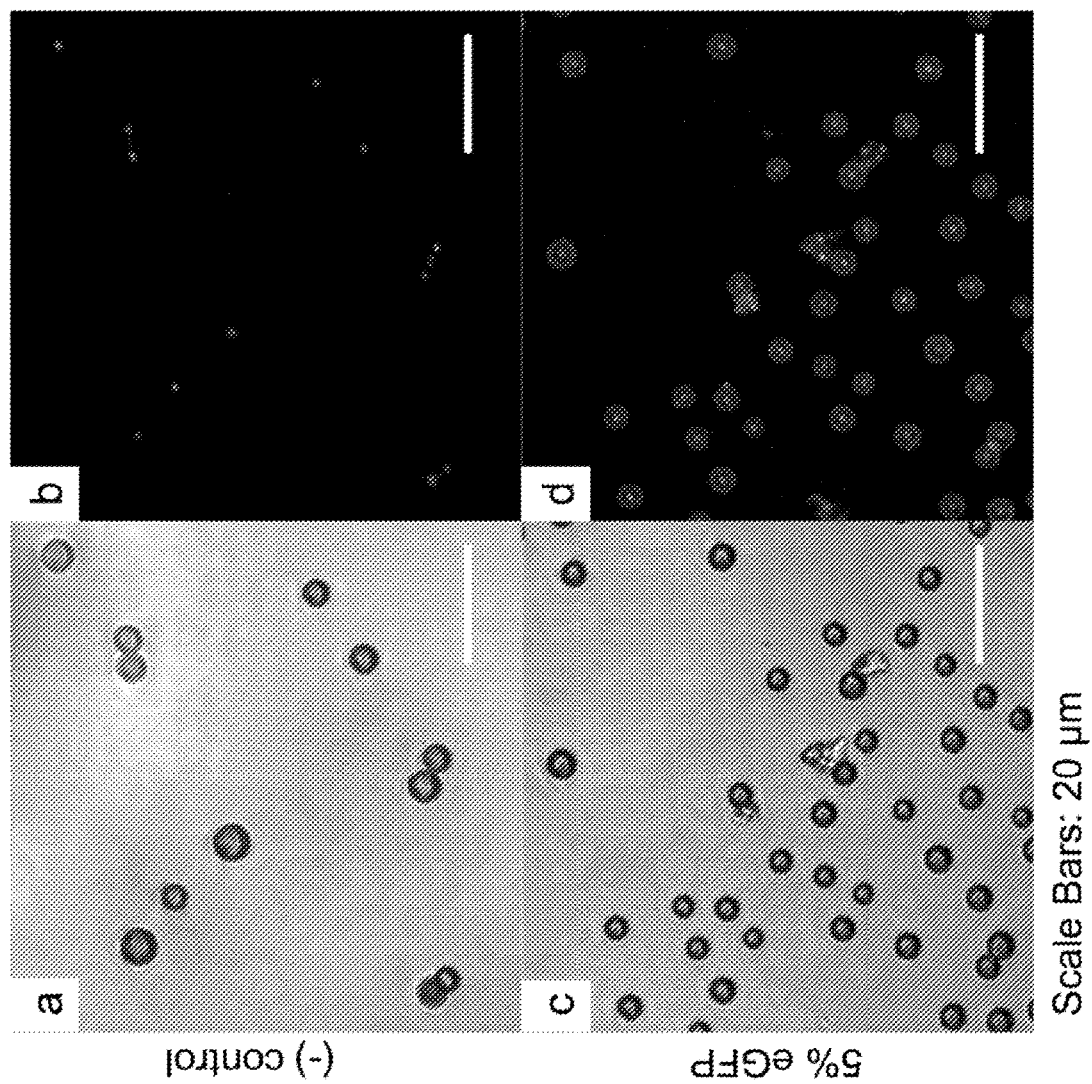
FIG. 13a is a confocal fluorescent microscopy image of bubbles produced with oleosin according to principles of the present invention.
FIG. 13b is a confocal fluorescent microscopy image of bubbles produced with oleosin according to principles of the present invention.
FIG. 13c is a confocal fluorescent microscopy image of bubbles produced with a blend containing the eGFP mutant according to principles of the present invention.
FIG. 13d is a confocal fluorescent microscopy image of bubbles produced with a blend containing the eGFP mutant according to principles of the present invention.

Since no major coalescence was observed between microbubbles occurring within the PDMS microfluidic device, while not intending to be bound to a particular theory, it is believed that these large bubbles likely form during transfer of the microbubbles from nozzle to a container via polyethylene tubing. Possibly, abrupt changes in dimensions and relative shear stress experienced by microbubbles between the PDMS device and the collection tube, as well as the lower speed at which the microbubbles travel in the polyethyelene tube before being released in a petri dish may lead to collision between bubbles and eventual coalescence. Another possibility is that these large bubbles have slightly different surface composition since they are observed to undergo dissolution when they are stored for an extended period, whereas the monodisperse bubbles that were originally generated at the nozzle do not dissolve completely over a long period of time. Highly monodisperse microbubbles are able to be collected, however, without any large bubbles if the produced bubbles are collected straight into a well that is positioned in the same plane as the microfluidic channel as shown in FIG. 11. These results show that even small perturbations can lead to disruption of microbubbles that are generated using microfluidic devices and extra care must be taken in collecting microbubbles for clinical applications since large bubbles in blood vessels can lead to serious problems such as embolism.

Microbubbles generated using the mixture of oleosin and $(PEO)_{78}$-$(PPO)_{30}$-$(PEO)_{78}$ (molar ratio of oleosin:triblock copolymer=1:18) were stable once collected. When microbubbles were collected and stored in water (microbubbles reside at the air-water interface due to their bouyancy), microbubble radius decreases by about 13% during the first few days and eventually ceased to shrink further. These microbubbles remain stable at least for 4 weeks as depicted by FIGS. 12a-d. SEM images depict the size of the microbubbles at collection (12(b)), over 7 days (12(c)), and after 24 hours (12(d)). The stability of these microbubbles does not depend on whether $N_2$ or $C_4F_8$ is used as the gas phase. In contrast, microbubbles generated solely with $(PEO)_{78}$-$(PPO)_{30}$-$(PEO)_{78}$ do not exhibit such excellent stability. These results indicate that oleosin plays a role in stabilizing the shell of microbubbles, which likely consists of a mixture of oleosin and $(PEO)_{78}$-$(PPO)_{30}$-$(PEO)_{78}$, to prevent complete dissolution or coalescence of microbubbles upon their collection. Similar examples, in which shells suppresses the dissolution of microbubbles, have been observed in microbubbles that have been stabilized with other types of proteins, nanoparticles or synthetic polymers.

As discussed above, one of the unique aspects of oleosin is that the molecular structure and thus the properties of the monolayer that contains this molecule can be engineered using recombinant protein technology. Recombinant protein technology allows for precise molecular engineering of proteins generated from microorganisms such as bacteria and thus can be used to generate oleosin species with different functionality and properties. To demonstrate that this molecule has such modularity, green fluorescent protein (GFP) mutant oleosin was expressed by fusing eGFP to the N-terminus of the 42-30G-63 oleosin. The modified oleosin genes are constructed using standard molecular biology techniques and cloned into the expression vector pBamUK. eGFP-functionalized oleosin is added to the aqueous phase during microbubble generation. It is evident that the microbubbles produced with the blend of the two oleosin species (pure at 1 mg mL$^{-1}$, mutant at 0.05 mg mL$^{-1}$) along with 10 mg mL$^{-1}$ $(PEO)_{78}$-$(PPO)_{30}$-$(PEO)_{78}$ has the eGFP mutant species incorporated in the bubble shell, whereas the microbubbles generated without the eGFP mutant species do not show any fluorescence. FIGS. 13a-d, which confirm this finding, depicts confocal fluorescent microscopy images of bubbles produced with (a and b) oleosin and (c and d) with a blend containing the eGFP mutant. Also fluorescence intensity was observed to be fairly uniform on the surface of the bubbles with no signs of phase separation, which has been observed on microbubbles that have been stabilized with mixture of phospholipids. These results indicate that oleosin with different functionalities can be generated and incorporated into the microbubble shell and that oleosin distributes uniformly on the surface of microbubbles.

Figure 14:
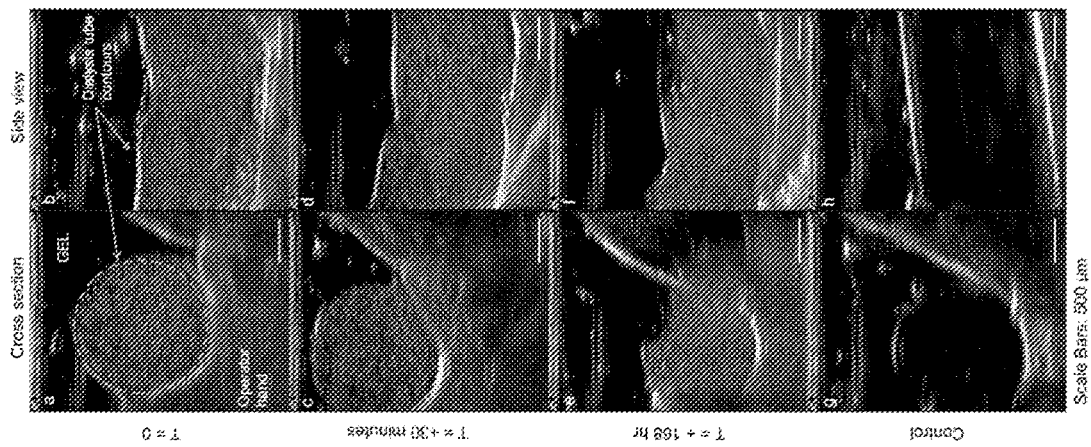
FIG. 14 is ultrasound sonography images of $C_4F_8$ microbubbles generated with a solution containing 1 mg mL$^{-1}$ oleosin and 10 mg mL$^{-1}$-$(PEO)_{78}$-$(PPO)_{30}$-$(PEO)_{78}$ over time according to principles of the present invention.

Echogenicity measurements were carried out using microbubbles generated with a solution containing 1 mg mL$^{-1}$ oleosin and 10 mg mL$^{-1}$ $(PEO)_{78}$-$(PPO)_{30}$-$(PEO)_{78}$. Microbubbles were collected directly in a ~3 cm long dialysis tubing with a diameter of 16 mm, which was sealed at one end and pre-filled with PBS solution containing 10 mg mL$^{-1}$ $(PEO)_{78}$-$(PPO)_{30}$-$(PEO)_{78}$. Microbubbles were flown directly into the dialysis tube from the PDMS device outlet using polyethylene tubing, which was submerged in the PBS solution. After collecting a desired amount of microbubbles, the tube was sealed on the other end to avoid introducing any air pockets and was stored in 50 mL centrifuge tubes filled with PBS solution containing 10 mg mL$^{-1}$ $(PEO)_{78}$-$(PPO)_{30}$-$(PEO)_{78}$. The tube was kept on a spinning wheel rotating at 60 rpm to induce continuous motions of the microbubbles and more importantly to remove large bubbles that may have been collected. The echogenicity of these microbubbles was tested using a broadband high-frequency ultrasound transducer at 7-15 MHz in brightness mode (B-mode). The microbubbles, with a radius of about 4 μm are acoustically active along the entire length of the dialysis tube as shown in FIG. 14. In contrast, a PBS solution containing 10 mg mL$^{-1}$ (PEO)$_{78}$-(PPO)$_{30}$-(PEO)$_{78}$ without any microbubbles does not show any acoustic signal, indicating that the oleosin-stabilized microbubbles are highly echogenic. Microbubbles remain acoustically responsive 30 min after the initial measurement and even one week after the first measurement, showing non-detectable changes in the signal brightness. These results indicate that these microbubbles stabilized with oleosin are highly stable and echogenic and thus could have significant potential for theranostic applications.

Example 5

Microbubbles Production and Characterization

The liquid phase containing the shell material included oleosin or a solution containing oleosin proteins and (PEO)$_{78}$-(PPO)$_{30}$-(PEO)$_{78}$ or (PEO)$_{100}$-(PPO)$_{65}$-(PEO)$_{100}$ diluted in phosphate-buffered saline (PBS) (pH 7.2, Sigma-Aldrich, St Luis, Mo., USA). The components were mixed together to the desired concentration. Microbubbles were generated using liquid phases containing different combinations of the three components. The liquid phase consisting of oleosin and (PEO)$_n$-(PPO)$_m$-(PEO)$_n$ triblock copolymers, at the optimal concentration dispersed in PBS were supplied to the microfluidic device using a Harvard Apparatus PHD Ultra syringe pump (Harvard Apparatus, Holliston, Mass.) at flow rates between 500 µL h$^{-1}$ to 1000 µL h$^{-1}$. To connect the channels to syringes, polyethylene tubing with an inner diameter of 0.38 mm and an outer diameter of 1.09 mm (BB31695-PE/2, Scientific Commodities Inc, Lake Havasu City, Ariz.) was used. The gas phase having 99.999% pure nitrogen gas (N$_2$, GTS Welco, Richmond, Va.) or octafluorocyclobutane (C$_4$F$_8$) (SynQuest Laboratories, Alachua, Fla.) was supplied to the device using a pressure regulator (Type 700, ControlAir Inc., Amhrest, N.H.) at pressures between 15 and 20 psi. Polyethylene tubing with an inner diameter of 0.86 mm and an outer diameter of 1.32 mm (BB31695-PE/5, Scientific Commodities Inc, Lake Havasu City, Ariz.) was used connect the channel to the pressure regulator. The membrane valve was actuated using a dual-valve pressure controller (PCD-100PSIG-D-PCV10, Alicat Scientific, Tucson, Ariz.) at pressure between 0 and 40 psi.

Microbubbles were produced by first applying a small pressure to the gas inlet (2-4 psi) immediately followed by injecting the liquid phase at the desired flow rate (500-1000 µL h$^{-1}$). The gas phase was then increased slowly until steady state of bubble generation is reached. Images of microbubbles production were captured using an inverted microscope (Nikon Diaphot 300, Melville, N.Y.) connected to a high speed Phantom V7 camera. For microbubbles that remained stable during generation and collection, long term stability was characterized by collecting microbubbles at the air-water interface in 35 mm petri dishes, acquiring images under a Carl Zeiss Axio Plan II upright microscope (Carl Zeiss Microscopy, Thornwood, N.Y.) connected to a QImaging Retiga 2000R camera. Microbubbles diameter variation over time was measured and images are analyzed using ImageJ (v 1.47v, NIH, USA).

Example 6

Ultrasound Imaging

Microbubbles for ultrasonic imaging were collected and imaged directly in 16 mm membrane dialysis bag, which was pre-filled with buffer solution and sealed at one end. After a desire amount of bubbles was collected, the tube was sealed at the other end carefully avoiding formations of air pockets. The collected microbubbles were imaged using a clinical ultrasound scanner HDI 5000 (Phillips/ATL, Bothell, Wash., USA) equipped with a broadband high-frequency ultrasound transducer at 7-15 MHz. Grayscale B-mode images were acquired with a mechanical index (MI) of 0.37 and 0.47 with focus between 0.5-1.5 cm and 1-2 cm, respectively. Time gain compensation (TGC) is fixed throughout the experiments.

Example 7

Figure 20:
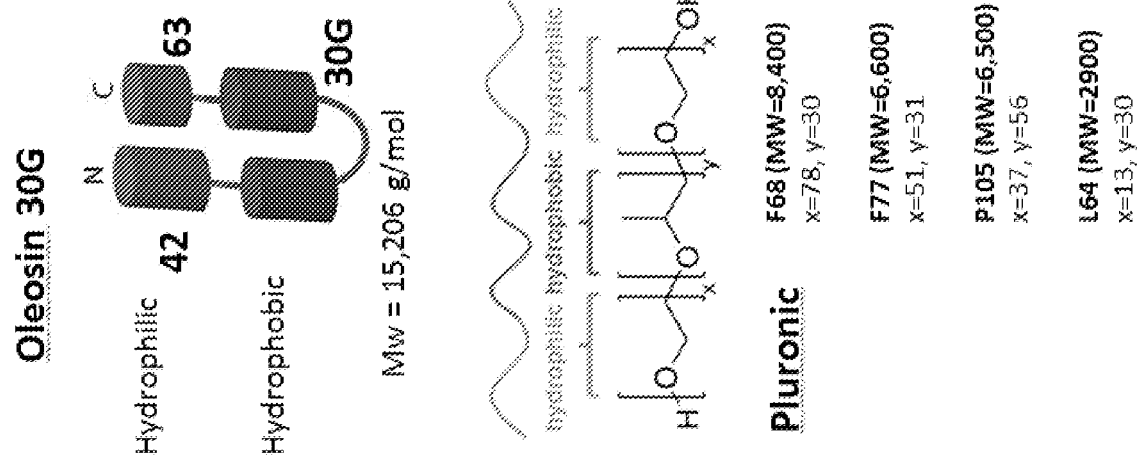
FIG. 20 illustrates physical properties of Oleosin 30G (MW=15,206 g/mol) and Pluronic® surfactants (F68 MW=8,400, F77 MW=6,600, P105 MW=6,500, L64 MW=2,900).

Tuning the Mechanical Properties of Recombinant Protein-Stabilized Microbubbles Using Triblock Copolymer Surfactants In this example, the mechanical properties of microbubbles stabilized with recombinant protein oleosin-30G were studied using micropipette aspiration technique. FIG. 20 illustrates physical properties of Oleosin 30G (MW=15,206 g/mol) and different Pluronic® surfactants (F68 MW=8,400, F77 MW=6,600, P105 MW=6,500, L64 MW=2,900).

As shown in FIG. 15a, microbubbles were generated by PDMS Hole Array Method, which is a new method for formulating air-filled microbubbles with tens-of-micrometer-size in diameter. This method has the most valuable merit of using a small amount of protein solutions, which lowers damage and contamination of high value biological samples. As shown in FIG. 15b, the average radius of the microbubbles (R$_{b,avg}$) was controlled by the PDMS hole sizes.

Figure 16:
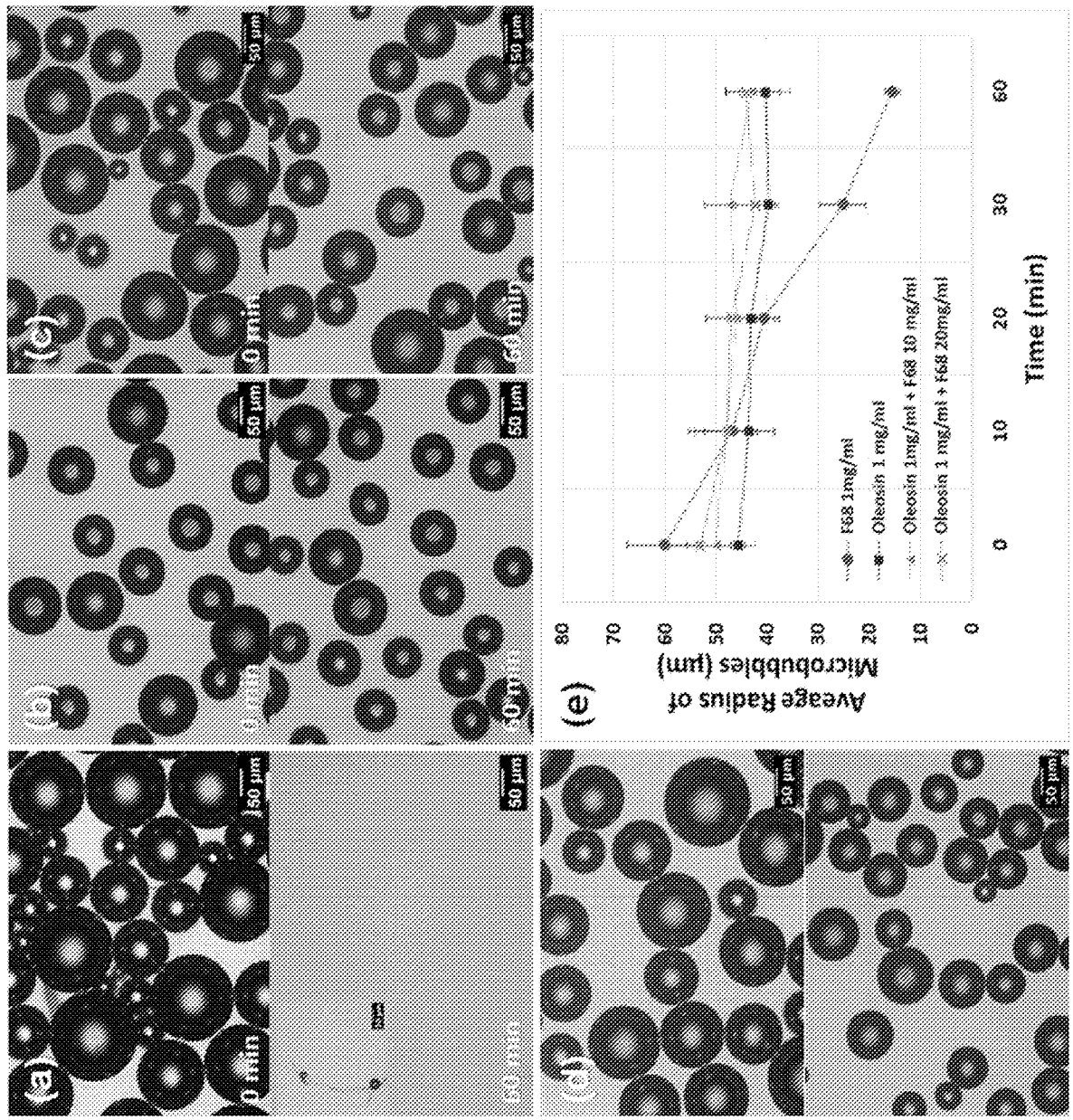
FIGS. 16a-d show microbubbles with different amounts of Pluronic® F68 and/or Oleosin-30G.
FIG. 16e shows changes in radius of microbubbles stabilized at different compositions as a function of time after collection.

As shown in FIGS. 16a-d, microbubbles were generated with different amounts of Pluronic® F68 and/or Oleosin-30G. FIG. 16a shows microbubbles with F68 at 1 mg/ml; FIG. 16b shows microbubbles with Oleosin-30G at 1 mg/ml; FIG. 16c shows microbubbles with Oleosin-30G at 1 mg/ml and F68 at 10 mg/ml; FIG. 16d shows microbubbles with Oleosin-30G at 1 mg/ml and F68 at 20 mg/ml. FIG. 16e shows changes in the radius of microbubbles stabilized at different compositions as a function of time after collection. The oleosin-30G plays a critical role to generate and stabilize the microbubbles.

Figure 17:
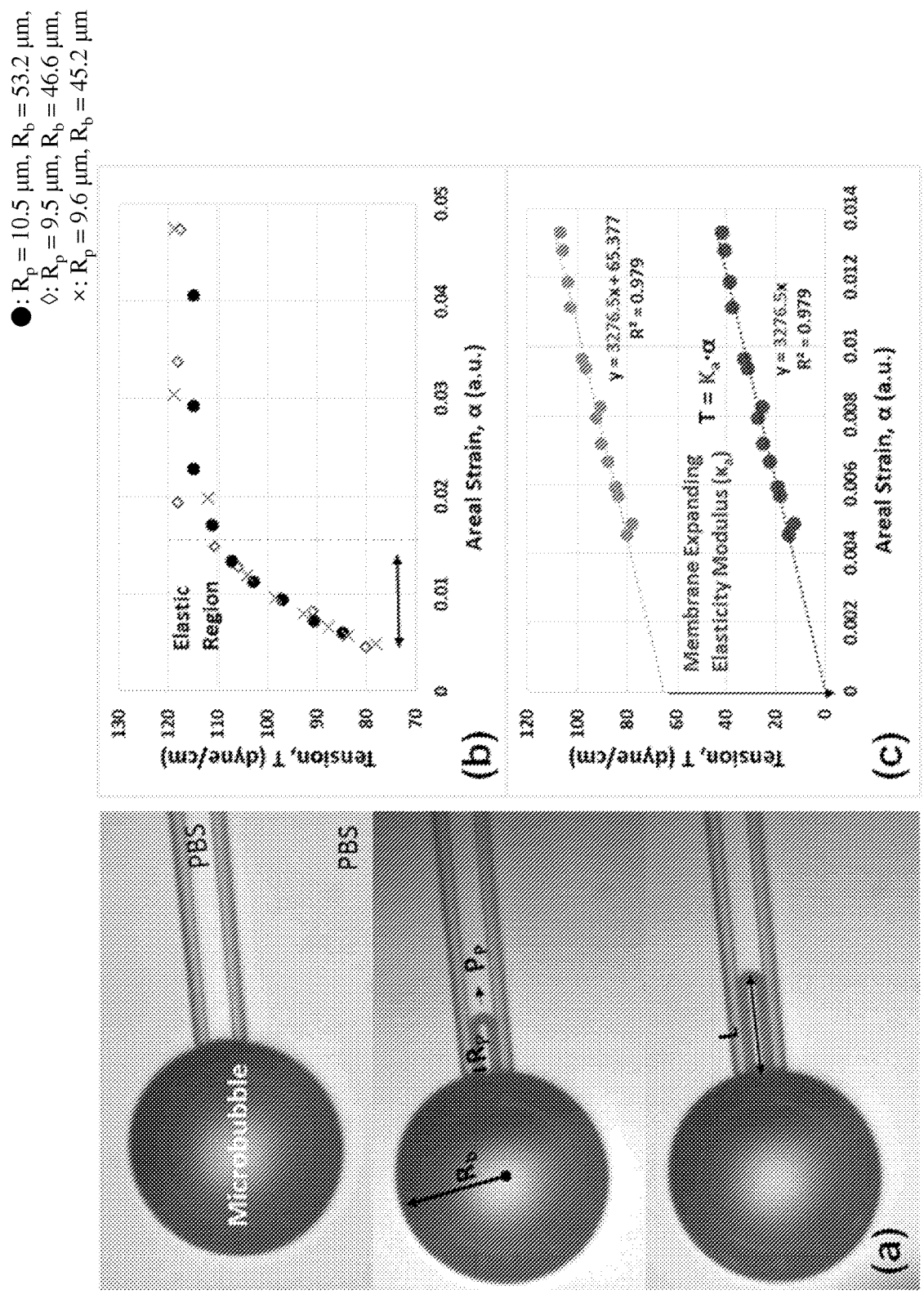
FIG. 17a illustrates micropipette aspiration of oleosin-30G-stabilized microbubbles with Pluronic® F68 (Oleosin-30G at 1 mg/ml+F68 at 10 mg/ml).
FIG. 17b shows representative aspiration results, exhibiting the typical stress-strain behavior of polymers.
FIG. 17c illustrates the Membrane Expanding Elasticity Modulus (Ka).
Figure 18:
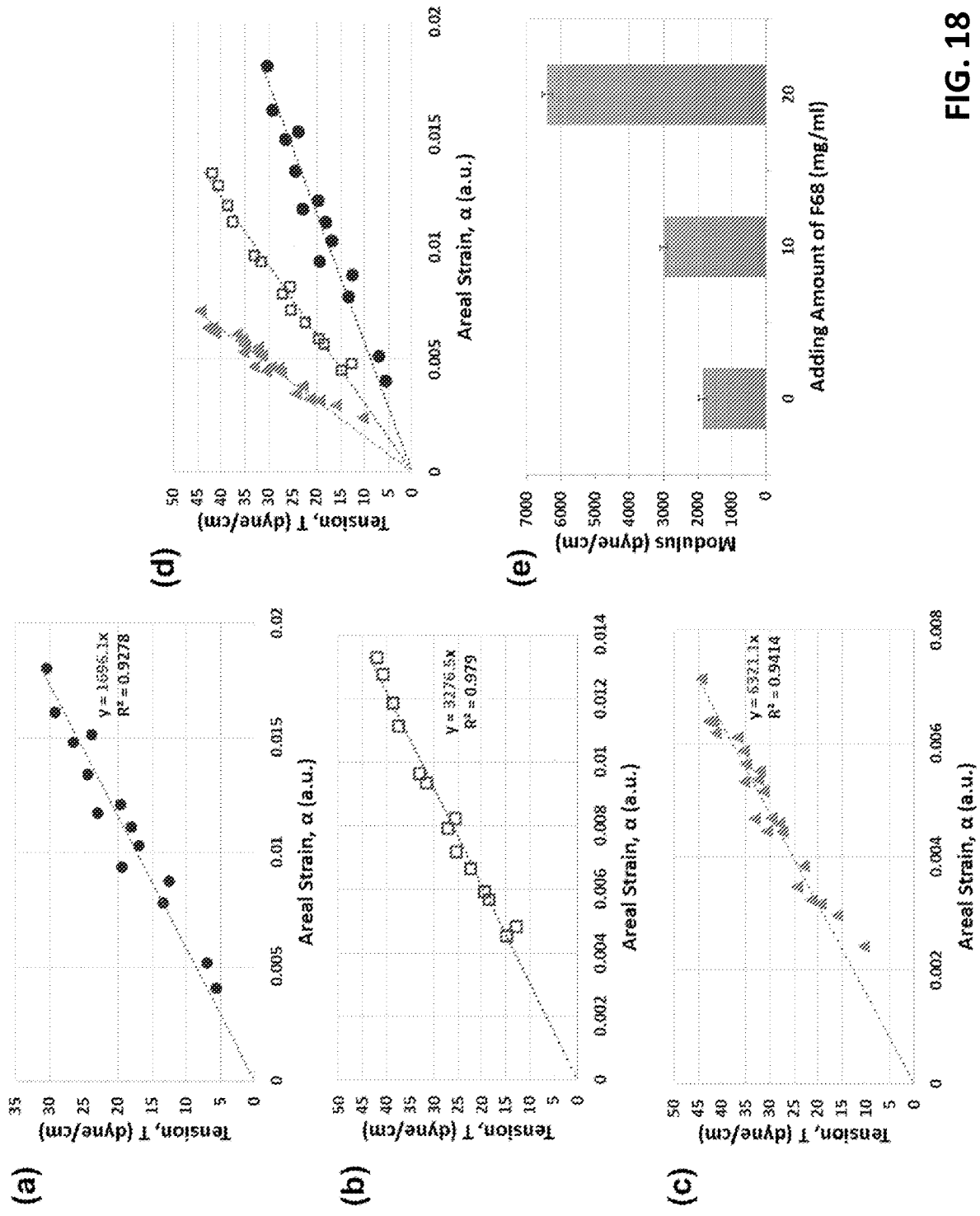
FIGS. 18a-e illustrate the effect of blending concentrations of a membrane sealing agent, Pluronic® F68.

FIG. 17a illustrates micropipette aspiration of oleosin-30G-stabilized microbubbles with Pluronic® F68 (Oleosin-30G at 1 mg/ml+F68 at 10 mg/ml). Negative pressure was needed to grab and hold microbubbles firmly with the micropipette.

FIGS. 18a-e illustrate the effect of blending different concentrations of a membrane sealing agent, Pluronic® F68, with Oleosin-30G. Pluronic® F68 has been used as a cell membrane sealing agent to protect cells against external shocks. The mean bursting membrane tension and the mean elastic area compressibility modulus of the cells increased with increasing amounts of Pluronic® F68.

Figure 19:
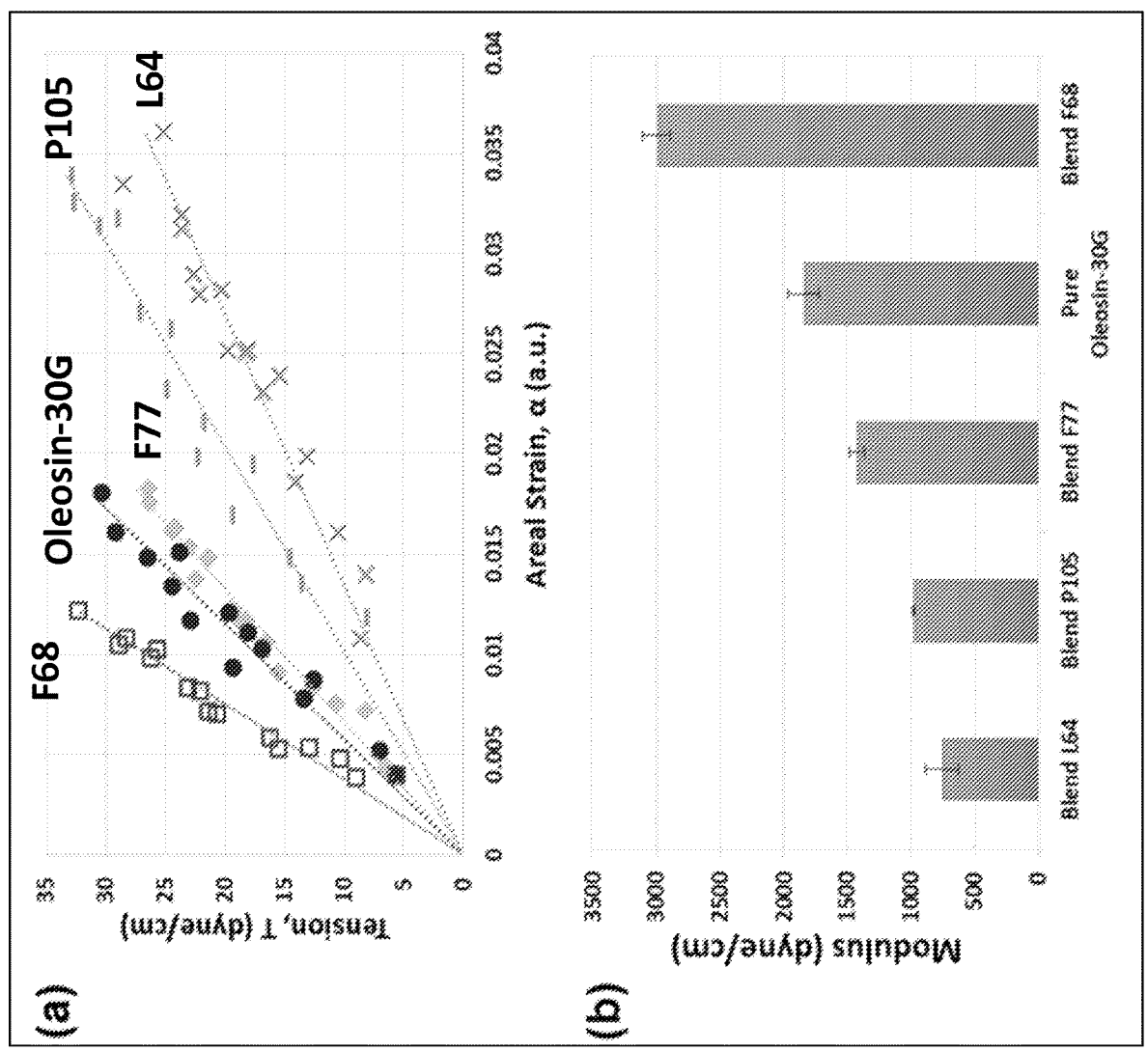
FIGS. 19a and 19b illustrate the effects on mechanical properties of Oleosin-30G microbubbles by adding different kinds of Pluronic® surfactants.

FIGS. 19a and 19b illustrate the effects on mechanical properties of Oleosin-30G microbubbles by adding different kinds of Pluronic® surfactants.

In this example, the real expansion modulus of the recombinant protein-shelled microbubbles was controlled by blending different types of triblock copolymer surfactants. The modulus of the oleosin-30G microbubbles increased by blending a cell membrane sealing agent, Pluronic® F68. The resulting a real expansion modulus was dependent on the F68 concentration. Furthermore, it was demonstrated that the Pluronic® triblock copolymers having shorter hydrophilic chains, as compared to hydrophobic chains, softened the oleosin-30G microbubble shells (see, e.g., FIG. 19b.)

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A microfluidic device for generating microbubbles, comprising:
   (a) a substrate that defines a plane;
   (b) a microfluidic channel system comprising a plurality of channels formed in the substrate and extending in the plane of the substrate along a surface of the substrate, the microfluidic channel system comprising:
      a plurality of fluid inlets,
      at least one bubble formation outlet, the at least one bubble formation outlet comprising a nozzle having an adjustable diameter, the adjustable diameter of the nozzle effecting control over the size of microbubbles exiting the nozzle, and
      a flow focusing junction in fluid communication with the plurality of fluid inlets and with the bubble formation outlet; and
   (c) a dynamically actuatable valve that encircles the nozzle and is adapted to inflate and dynamically constrict the nozzle of the bubble formation outlet so as to change the adjustable diameter of the nozzle, wherein the dynamically actuatable valve and the microfluidic channel system lie in the plane of the substrate.

2. The microfluidic device of claim 1, wherein a first fluid inlet of the plurality of fluid inlets comprises an inlet for a gas, and a second fluid inlet of the plurality of fluid inlets comprises an inlet for a liquid.

3. The microfluidic device of claim 1, wherein the first fluid inlet and the second fluid discharge into the flow focusing junction, and wherein the bubble formation outlet is disposed at the flow focusing junction.

4. The microfluidic device of claim 1, wherein the dynamically actuated valve is a fluid-actuated valve.

5. The microfluidic device of claim 1 comprising more than one bubble formation outlet, wherein each of the one or more bubble formation outlets comprises a respective nozzle having an adjustable diameter.

6. The microfluidic device of claim 4, wherein the microfluidic channel system and the valve define a direction of flow in the same plane.

7. The microfluidic device of claim 6 wherein the substrate comprises a polymer.

8. The microfluidic device of claim 7, wherein the polymer comprises polydimethylsiloxane, a polyacrylamide, a polyacrylate, a polymethacrylate or a mixture thereof.

9. The device of claim 1, further comprising at least one valve control channel formed in the substrate and extending in the plane of the substrate along a surface of the substrate, wherein the at least one valve control channel is in fluid communication with the valve, and wherein exertion of fluid in the at least one valve control channel acts to inflate the dynamically actuated valve so as to constrict the diameter of the nozzle.

* * * * *

UNITED STATES PATENT AND TRADEMARK OFFICE
CERTIFICATE OF CORRECTION

Page 1 of 2

PATENT NO. : 11,065,348 B2
APPLICATION NO. : 15/320177
DATED : July 20, 2021
INVENTOR(S) : Daeyeon Lee et al.

It is certified that error appears in the above-identified patent and that said Letters Patent is hereby corrected as shown below:

In the Specification

In Brief Description of the Drawings
Under Column No. 4, Line no. 31, Replace:
"a real"
With:
-- areal --

In Brief Description of the Drawings
Under Column No. 4, Line no. 33, Replace:
"a real"
With:
-- areal --

In Brief Description of the Drawings
Under Column No. 4, Line no. 35, Replace:
"a real"
With:
-- areal --

In Brief Description of the Drawings
Under Column No. 4, Line no. 43, Replace:
"a real"
With:
-- areal --

DETAILED DESCRIPTION OF THE INVENTION

Under Column No. 7, Line no. 47, Replace:

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*

"per fluorocarbon"
With:
-- perfluorocarbon --

Example 7 - Tuning the Mechanical Properties of Recombinant Protein-Stabilized Microbubbles Using Triblock Copolymer Surfactants Under Column No. 18, Line no. 63, Replace:
"a real"
With:
-- areal --